(12) United States Patent
Ragini et al.

(10) Patent No.: US 7,601,438 B2
(45) Date of Patent: Oct. 13, 2009

(54) CYCLOMETALATED TRANSITION METAL COMPLEX AND ORGANIC ELECTROLUMINESCENT DISPLAY DEVICE USING THE SAME

(75) Inventors: Das Rupasree Ragini, Suwon-si (KR); Seok Chang, Daejeon-si (KR); Yi-Yeol Lyu, Yongin-si (KR); Eun-Sil Han, Yongin-si (KR); Young-Hun Byun, Yongin-si (KR); Lyong-Sun Pu, Suwon-si (KR); Jong-Hyoup Lee, Seoul (KR)

(73) Assignee: Samsung Mobile Display Co., Ltd., Yongin, Gyunggi-Do (KR)

( * ) Notice: Subject to any disclaimer, the term of this patent is extended or adjusted under 35 U.S.C. 154(b) by 688 days.

(21) Appl. No.: 11/219,820

(22) Filed: Sep. 7, 2005

(65) Prior Publication Data

US 2006/0078760 A1    Apr. 13, 2006

(30) Foreign Application Priority Data

Oct. 11, 2004    (KR) .................... 10-2004-0081060

(51) Int. Cl.
*H01L 51/54* (2006.01)
*C09K 11/06* (2006.01)

(52) U.S. Cl. .................. 428/690; 428/917; 313/504; 313/506; 257/E51.044; 548/101; 548/103; 548/108; 548/402; 546/4; 546/10

(58) Field of Classification Search .............. None
See application file for complete search history.

(56) References Cited

U.S. PATENT DOCUMENTS

| | | | |
|---|---|---|---|
| 2001/0019782 A1* | 9/2001 | Igarashi et al. | 428/690 |
| 2002/0048689 A1 | 4/2002 | Igarashi et al. | |
| 2002/0064681 A1 | 5/2002 | Takiguchi et al. | |
| 2002/0134984 A1 | 9/2002 | Igarashi | |
| 2002/0182441 A1 | 12/2002 | Lamansky et al. | |
| 2007/0048546 A1* | 3/2007 | Ren | 428/690 |

FOREIGN PATENT DOCUMENTS

WO    WO 02/15645    2/2002

OTHER PUBLICATIONS

An article "Highly efficient phosphorescent emission from organic electroluminescent devices" written by Baldo, et al. published in Nature, vol. 395 pp. 151-154 on Sep. 10, 1998.

* cited by examiner

*Primary Examiner*—Marie R. Yamnitzky
(74) *Attorney, Agent, or Firm*—Robert E. Bushnell, Esq.

(57) ABSTRACT

A cyclometalated transition metal complex exhibiting phosphorescence with high efficiency and an organic electroluminescent display device using the same are provided. This transition metal complex can be used in forming an organic film of an organic electroluminescent display device. The transition metal complex can emit light at the wavelength range of 400 to 650 nm. Further, the complex can emit white light by using a green light emitting material or a red light emitting material together.

19 Claims, 6 Drawing Sheets

US 7,601,438 B2

CYCLOMETALATED TRANSITION METAL COMPLEX AND ORGANIC ELECTROLUMINESCENT DISPLAY DEVICE USING THE SAME

CLAIM OF PRIORITY

This application claims the benefit of Korean Patent Application No. 10-2004-0081060, filed on Oct. 11, 2004, in the Korean Intellectual Property Office, the disclosure of which is incorporated herein in its entirety by reference.

BACKGROUND OF THE INVENTION

1. Field of the Invention

The present invention relates to a cyclometalated transition metal complex and an organic electroluminescent display device using the same, and more particularly, to a cyclometalated transition metal complex that can emit light at a wavelength range from the blue region to the red region from triplet metal-to-ligand charge-transfer ($^3$MLCT) state, and an organic electroluminescent display device that applies the complex as an organic film forming material.

2. Description of the Related Art

An organic electroluminescent display device (organic electroluminescence (EL) display device) is an active light-emitting display device employing the phenomenon that when an electric current is applied to a thin film (hereinafter referred to as "organic film") composed of a fluorescent or phosphorescent organic compound, the fluorescent or the phosphorescent organic compound emits light in response to the recombination of electrons and holes in the organic film. The display device is light, has a structure of which the components are simple and its manufacturing process is simple, and ensures wide view angle with high image quality. Further, the display has the electrical properties suitable for portable electronic devices, since it can embody completely high color purity and moving picture, and can be driven with low power consumption and low voltage.

A general organic electroluminescent display device has a structure that has an anode formed at the upper part of a substrate, and a hole transporting layer, a light emitting layer, an electron transporting layer and a cathode sequentially formed at the upper part of the anode. Herein, the hole-transporting layer, the light emitting layer and the electron-transporting layer are organic films composed of organic compounds. The driving principle for the organic electroluminescent display device having such a structure is as follows. When voltage is applied between the anode and the cathode, a hole injected from an anode is migrated to a light-emitting layer via a hole-transporting layer. Meanwhile, an electron is injected from a cathode into a light-emitting layer via an electron-transporting layer, and carriers are recombined at the area of the light-emitting layer to form an exciton. The exciton emits light with a wavelength corresponding to a band gap of the material when the exciton decays radiatively.

The light emitting layer-forming materials are classified into a fluorescent material using singlet excitons and a phosphorescent material using triplet excitons, according to their light-emitting mechanism. The light emitting layer is formed of the fluorescent or phosphorescent material alone or an appropriate host material doped with the fluorescent or phosphorescent material, and as electrons are excited, singlet excitons and triplet excitons are formed in the host. Herein, the statistic-forming ratio of the singlet excitons to the triplet excitons is 1:3.

The organic electroluminescent display device using a fluorescent material as a light emitting layer-forming material has a disadvantage that the triplet excitons formed in the host are wasted, while the device using a phosphorescent material as a light emitting layer-forming material has an advantage that both of the singlet excitons and the triplet excitons can be used, and thus the internal quantum efficiency can reach 100% (Baldo, et al., Nature, Vol. 395, 151-154, 1998). Accordingly, the phosphorescent material can possess even higher light emitting efficiency when a phosphorescent material is used as a light emitting layer-forming material than when a fluorescent material is used.

When a heavy metal such as Ir, Pt, Rh, Pd, etc. is incorporated into an organic molecule, triplet state and singlet state are mixed through spin-orbital coupling occurred by the heavy metal atom effect. Due to this, the transition that had been blocked is possible, and the phosphorescence can be occurred efficiently even at room temperature.

Recently, a green material or a red material with high efficiency employing the phosphorescence of which the internal quantum efficiency reaches 100% was developed.

Although transition metal compounds comprising transition metals such as an iridium, a platinum, etc. as a highly efficient luminescent material employing phosphorescence are reported, the materials that satisfy the properties required for realizing a full color display with high efficiency or white light emitting with low power consumption are limited to the green and red regions, and a phosphorescent material suitable for the blue region is not developed. For such reason, there is an obstacle in developing a phosphorescent full color device.

To solve such problems, a blue light emitting material is developing (WO02/15645 A1, U.S. Patent Publication No. 2002/0064681 A1). Further, an organic metal complex, incorporating a bulky functional group that can make the HOMO-LUMO difference large by changing the molecular geometry, or a functional group that has a strong ligand field (e.g., cyano group), was developed. Besides, an iridium complex represented by formula Ir(ppy)$_2$P(ph)$_3$Y (wherein Y=Cl or CN) (U.S. Patent Publication No. 2002/0182441 A1), and an iridium (III) complex having a cyclometalated ligand, a chelating diphosphine, a chlorine and a cyano group (U.S. Patent Publication No. 2002/0048689 A1) were developed.

Further, the US Patent Publication No. 2002/0134984 discloses a cyclometalated transition metal complex comprised of nitrogen atoms and carbon atoms, and an organic electroluminescent display device comprising the same.

However, all of the above materials do not show satisfactory properties in terms of color purity, light emitting efficiency and lifetime, etc.

SUMMARY OF THE INVENTION

It is therefore an object of the present invention to provide an improved organic film forming material.

It is also an object of the present invention to provide an improved organic electroluminescent display device The present invention provides a cyclometalated transition metal complex that can emit light at a wavelength range from the blue region to the red region more efficiently by triplet metal-to-ligand charge-transfer ($^3$MLCT) state.

The present invention also provides an organic electroluminescent display device that can emit light at a wavelength range from the blue region to the red region more efficiently.

According to an aspect of the present invention, there is provided a cyclometalated transition metal complex represented by the formula I below:

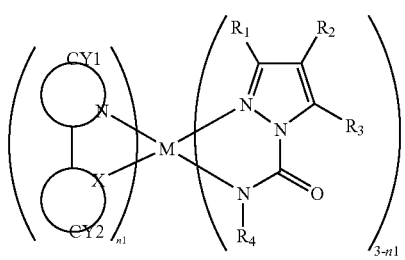

(I)

wherein M is a transition metal;
each of $R_1$, $R_2$, $R_3$ and $R_4$ is a substituent or a hydrogen atom;
X is N or C;
each of CY1 and CY2 is an aromatic ring or an aliphatic ring; and
n1 is 1 or 2.

According to another aspect of the present invention, there is provided an organic electroluminescent display device including an organic film between a pair of electrodes, wherein the organic film comprises a cyclometalated transition metal complex represented by the formula I.

The $R_1$, $R_2$, $R_3$ and $R_4$ may be independently a hydrogen atom, or any substituent selected from the group consisting of an alkyl group (preferably $C_1$-$C_{30}$, more preferably $C_1$-$C_{20}$, most preferably $C_1$-$C_{10}$), an alkenyl group (preferably $C_2$-$C_{30}$, more preferably $C_2$-$C_{20}$, most preferably $C_2$-$C_{10}$), an alkynyl group (preferably $C_2$-$C_{30}$, more preferably $C_2$-$C_{20}$, most preferably $C_2$-$C_{10}$), an aryl group (preferably $C_6$-$C_{30}$, more preferably $C_6$-$C_{20}$, most preferably $C_6$-$C_{12}$), an amino group (preferably $C_0$-$C_{30}$, more preferably $C_0$-$C_{20}$, most preferably $C_0$-$C_{10}$), an alkoxy group (preferably $C_1$-$C_{30}$, more preferably $C_1$-$C_{20}$, most preferably $C_1$-$C_{10}$), an aryloxy group (preferably $C_6$-$C_{30}$, more preferably $C_6$-$C_{20}$, most preferably $C_6$-$C_{12}$), a heterocyclicoxy group (preferably $C_1$-$C_{30}$, more preferably $C_1$-$C_{20}$, most preferably $C_1$-$C_{12}$), an acyl group (preferably $C_1$-$C_{30}$, more preferably $C_1$-$C_{20}$, most preferably $C_1$-$C_{12}$), an alkoxycarbonyl group (preferably $C_2$-$C_{30}$, more preferably $C_2$-$C_{20}$, most preferably $C_2$-$C_{12}$), an aryloxycarbonyl group (preferably $C_7$-$C_{30}$, more preferably $C_7$-$C_{20}$, most preferably $C_7$-$C_{12}$), an acyloxy group (preferably $C_2$-$C_{30}$, more preferably $C_2$-$C_{20}$, most preferably $C_2$-$C_{10}$), an acylamino group (preferably $C_2$-$C_{30}$, more preferably $C_2$-$C_{20}$, most preferably $C_2$-$C_{10}$), an alkoxycarbonylamino group (preferably $C_2$-$C_{30}$, more preferably $C_2$-$C_{20}$, most preferably $C_2$-$C_{12}$), an aryloxycarbonylamino group (preferably $C_7$-$C_{30}$, more preferably $C_7$-$C_{20}$, most preferably $C_7$-$C_{12}$), a sulfonylamino group (preferably $C_1$-$C_{30}$, more preferably $C_1$-$C_{20}$, most preferably $C_1$-$C_{12}$), a sulfamoyl group (preferably $C_0$-$C_{30}$, more preferably $C_0$-$C_{20}$, most preferably $C_0$-$C_{12}$), a carbamoyl group (preferably $C_1$-$C_{30}$, more preferably $C_1$-$C_{20}$, most preferably $C_1$-$C_{12}$), an alkylthio group (preferably $C_1$-$C_{30}$, more preferably $C_1$-$C_{20}$, most preferably $C_1$-$C_{12}$), an arylthio group (preferably $C_6$-$C_{30}$, more preferably $C_6$-$C_{20}$, most preferably $C_6$-$C_{12}$), a heterocyclicthio group (preferably $C_1$-$C_{30}$, more preferably $C_1$-$C_{20}$, most preferably $C_1$-$C_{12}$), a sulfonyl group (preferably $C_1$-$C_{30}$, more preferably $C_1$-$C_{20}$, most preferably $C_1$-$C_{12}$), a sulfinyl group (preferably $C_1$-$C_{30}$, more preferably $C_1$-$C_{20}$, most preferably $C_1$-$C_{12}$), an ureido group (preferably $C_1$-$C_{30}$, more preferably $C_1$-$C_{20}$, most preferably $C_1$-$C_{12}$), a phophoramide group (preferably $C_1$-$C_{30}$, more preferably $C_1$-$C_{20}$, most preferably $C_1$-$C_{12}$), a hydroxyl group, a mercapto group, a halogen atom, a cyano group, a sulfo group, a carboxyl group, a nitro group, a hydroxamic group, a sulfino group, a hydrazino group, an imino group, a heterocyclic group (preferably $C_1$-$C_{30}$, more preferably $C_1$-$C_{12}$), a silyl group (preferably $C_3$-$C_{40}$, more preferably $C_3$-$C_{30}$, most preferably $C_3$-$C_{24}$) and a silyloxy group (preferably $C_3$-$C_{40}$, more preferably $C_3$-$C_{30}$, most preferably $C_3$-$C_{24}$).

The cyclometalated transition metal complex represented by the formula I may be any one of the compounds represented by Formulae II through X below:

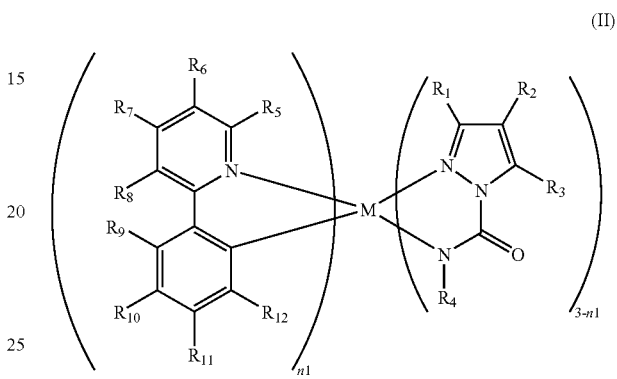

(II)

wherein each of $R_1$, $R_2$, $R_3$, $R_4$, $R_5$, $R_6$, $R_7$, $R_8$, $R_9$, $R_{10}$, $R_{11}$, and $R_{12}$ is a substituent or a hydrogen atom;
M is a transition metal; and
n1 is 1 or 2.

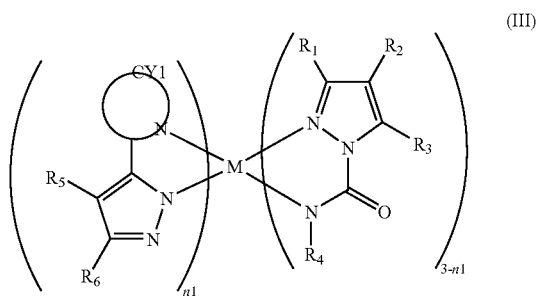

(III)

wherein each of $R_1$, $R_2$, $R_3$, $R_4$, $R_5$, and $R_6$ is a substituent or a hydrogen atom;
M is a transition metal;
n1 is 1 or 2; and
CY1 is an aromatic ring or an aliphatic ring.

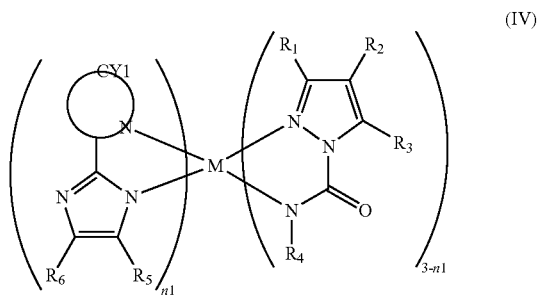

(IV)

wherein each of $R_1$, $R_2$, $R_3$, $R_4$, $R_5$, and $R_6$ is a substituent or a hydrogen atom;

M is a transition metal;
n1 is 1 or 2; and
CY1 is an aromatic ring or an aliphatic ring.

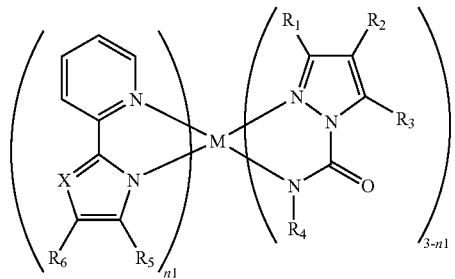

(V)

wherein each of $R_1$, $R_2$, $R_3$, $R_4$, $R_5$, and $R_6$ is a substituent or a hydrogen atom;

M is a transition metal;
X is C, N, O, S or P; and
n1 is 1 or 2.

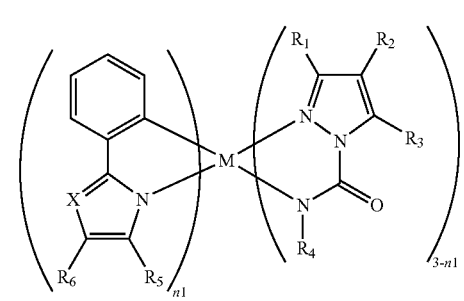

(VI)

wherein each of $R_1$, $R_2$, $R_3$, $R_4$, $R_5$, and $R_6$ is a substituent or a hydrogen atom;

M is a transition metal;
X is C, N, O, S or P; and
n1 is 1 or 2.

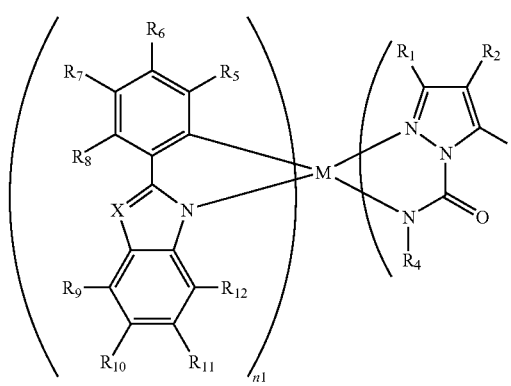

(VII)

wherein each of $R_1$, $R_2$, $R_3$, $R_4$, $R_5$, $R_6$, $R_7$, $R_8$, $R_9$, $R_{10}$, $R_{11}$, and $R_{12}$ is a substituent or a hydrogen atom;

M is a transition metal;
X is C, N, O, S or P; and
n1 is 1 or 2.

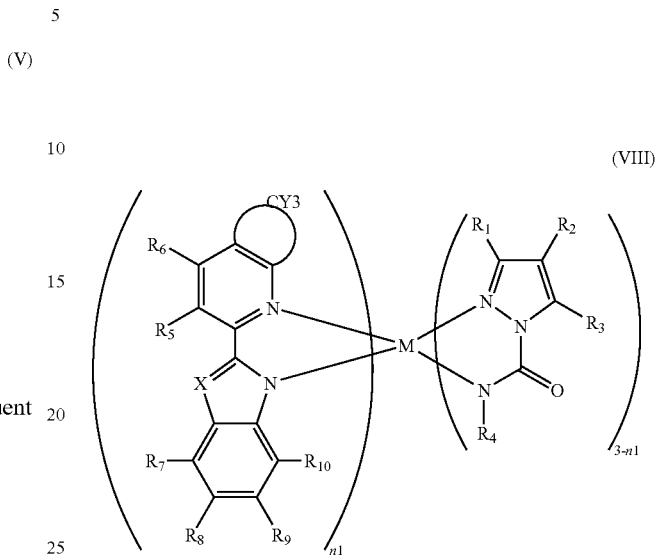

(VIII)

wherein each of $R_1$, $R_2$, $R_3$, $R_4$, $R_5$, $R_6$, $R_7$, $R_8$, $R_9$, and $R_{10}$ is a substituent or a hydrogen atom;

M is a transition metal;
X is C, N, O, S or P;
CY3 is an aromatic ring or an aliphatic ring; and
n1 is 1 or 2.

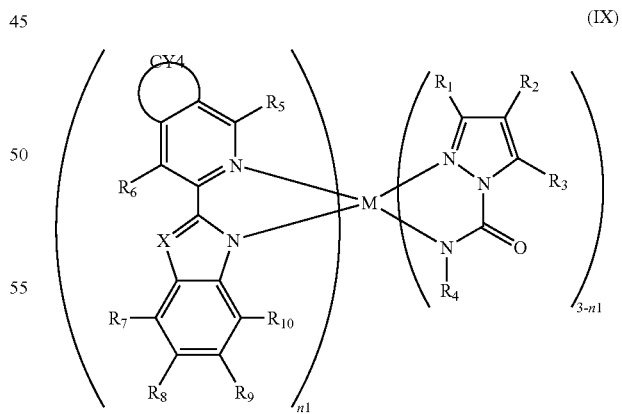

(IX)

wherein each of $R_1$, $R_2$, $R_3$, $R_4$, $R_5$, $R_6$, $R_7$, $R_8$, $R_9$, and $R_{10}$ is a substituent or a hydrogen atom;

M is a transition metal;

X is C, N, O, S or P;

CY4 is an aromatic ring or an aliphatic ring, and n1 is 1 or 2.

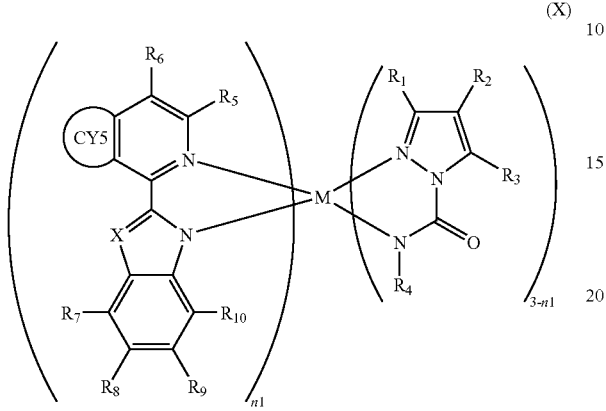

(X)

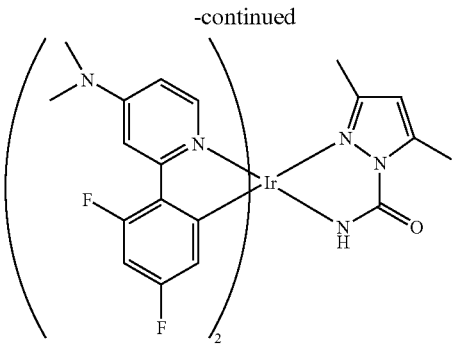

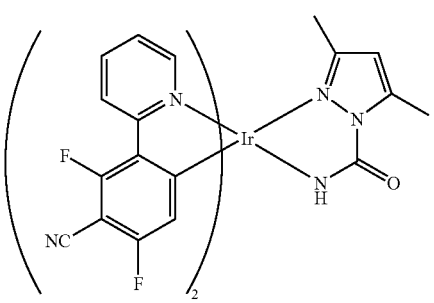

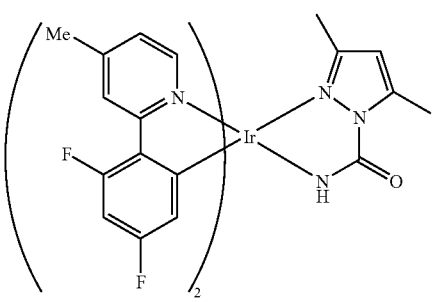

wherein each of $R_1, R_2, R_3, R_4, R_5, R_6, R_7, R_8, R_9,$ and $R_{10}$ is a substituent or a hydrogen atom;

M is a transition metal;

X is C, N, O, S or P;

CY5 is an aromatic ring or an aliphatic ring; and n1 is 1 or 2.

In the formulae II through X, $R_1, R_2, R_3, R_4, R_5, R_6, R_7, R_8, R_9, R_{10}, R_{11},$ and $R_{12}$ may include the substituents defined in $R_1, R_2, R_3,$ and $R_4$ of the formula I.

In the formulae I through X, CY1, CY2, CY3, CY4 and CY5 may include aromatic hydrocarbon rings such as a benzene ring, a naphthalene ring, a quinoxaline and an anthracene ring; aromatic heterocycles such as a pyridine ring, a pyrazine ring, a quinoline ring, a furan ring and a thiophene ring; aliphatic hydrocarbon rings such as a cyclohexane ring; and aliphatic heterocycles such as a pyrane ring.

In the formula I, the transition metal M may be Ru, Rh, Os, Ir, Pt or Au.

The cyclometalated transition metal complex according to an embodiment is preferably one of the compounds represented by the formulae below:

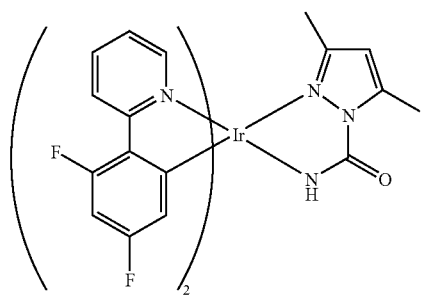

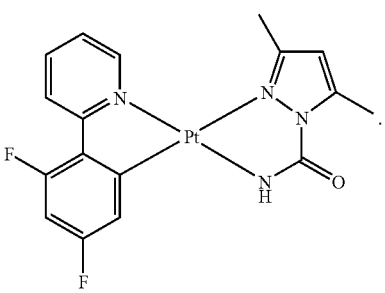

According to another aspect of the present invention, an organic electroluminescent display device is constructed with a pair of electrodes and an organic film between the pair of electrodes, the organic film including a transition metal complex having a transition metal and a pyrazolecarboxamide ligand connected to the transition metal.

The cyclometalated transition metal complex can emit light at a wavelength range of 400 nm to 680 nm. The light emitting diode employing such an organic metal complex may be used in light source illumination for displaying full color, backlight, an outdoor bulletin board, optical communication, and interior decoration, etc.

BRIEF DESCRIPTION OF THE DRAWINGS

A more complete appreciation of the present invention, and many of the above and other features and advantages of the present invention, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1:
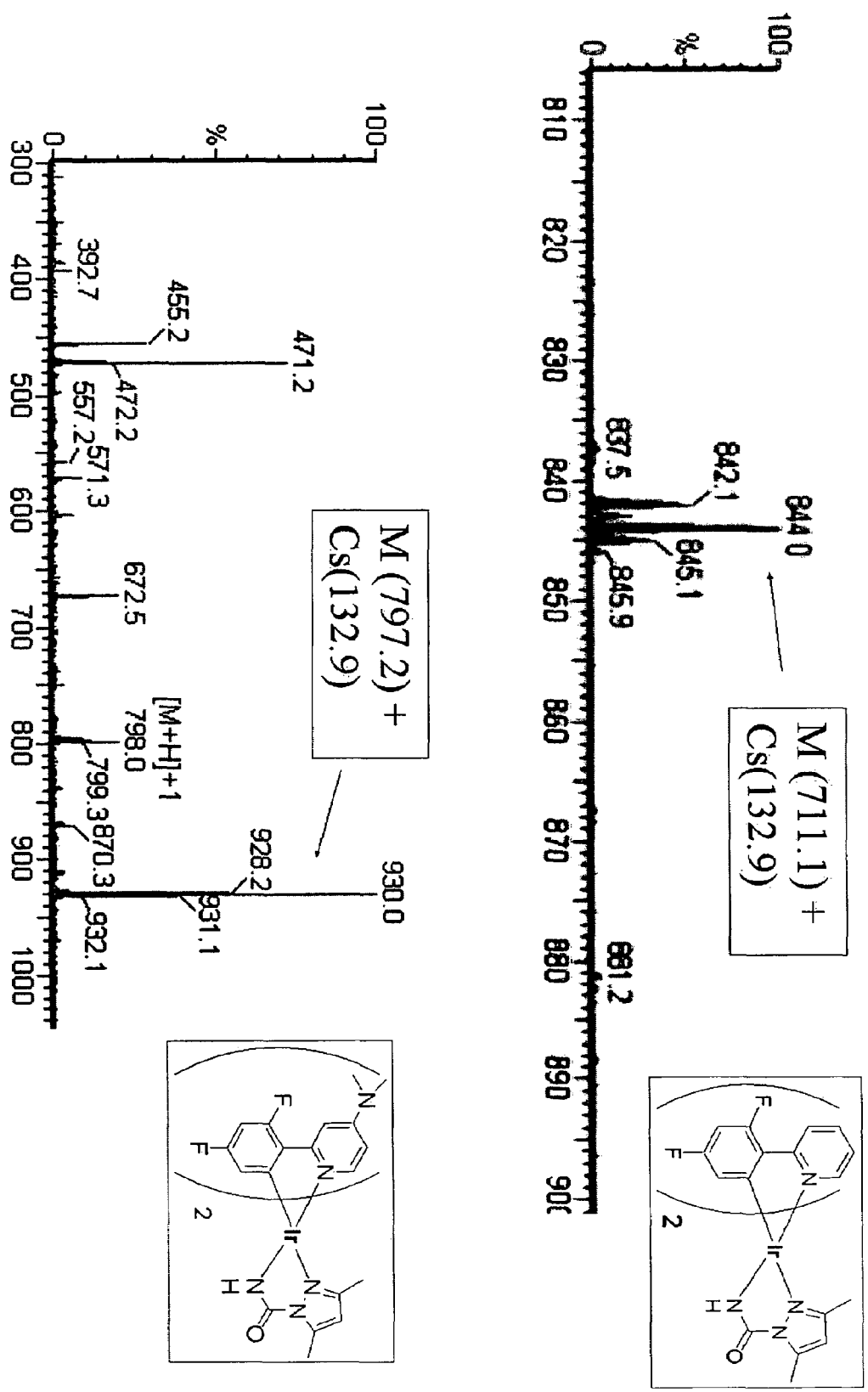
FIG. 1 is a mass spectrum of the compounds according to the examples 1 and 3 of the present invention.

The present invention will now be described more fully hereinafter with reference to the accompanying drawings, in which preferred embodiments of the invention are shown. This invention may, however, be embodied in many different forms and should not be construed as being limited to the embodiments set forth herein. Rather, these embodiments are provided so that this disclosure will be thorough and complete, and will fully convey the scope of the invention to those skilled in the art. Like numbers refer to like elements throughout the specification.

The present invention provides a cyclometalated transition metal complex that can emit light at a wavelength range from the blue region to the red region more efficiently by triplet metal-to-ligand charge-transfer ($^3$MLCT) state.

According to an aspect of the present invention, there is provided a cyclometalated transition metal complex represented by the formula I below:

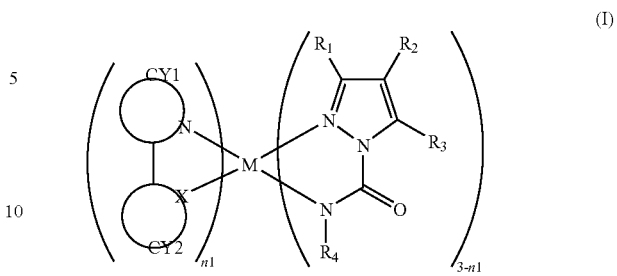

wherein M is a transition metal;
each of $R_1$, $R_2$, $R_3$ and $R_4$ is a substituent or a hydrogen atom;
X is N or C;
each of CY1 and CY2 is an aromatic ring or an aliphatic ring; and
n1 is 1 or 2.

According to another aspect of the present invention, there is provided an organic electroluminescent display device including an organic film between a pair of electrodes, wherein the organic film comprises a cyclometalated transition metal complex represented by the formula I.

A cyclometalated transition metal complex according to the present invention can emit blue light with high performance and efficiency by including a non-carbon coordinating chelating ligand.

The cyclometalated transition metal complex according to the present invention is characterized in that a pyrazolecarboxamide ligand is connected to a transition metal.

The $R_1$, $R_2$, $R_3$ and $R_4$ may be independently a hydrogen atom, or any substituent selected from the group consisting of an alkyl group (preferably $C_1$-$C_{30}$, more preferably $C_1$-$C_{20}$, most preferably $C_1$-$C_{10}$), an alkenyl group (preferably $C_2$-$C_{30}$, more preferably $C_2$-$C_{20}$, most preferably $C_2$-$C_{10}$), an alkynyl group (preferably $C_2$-$C_{30}$, more preferably $C_2$-$C_{20}$, most preferably $C_2$-$C_{10}$), an aryl group (preferably $C_6$-$C_{30}$, more preferably $C_6$-$C_{20}$, most preferably $C_6$-$C_{12}$), an amino group (preferably $C_0$-$C_{30}$, more preferably $C_0$-$C_{20}$, most preferably $C_0$-$C_{10}$), an alkoxy group (preferably $C_1$-$C_{30}$, more preferably $C_1$-$C_{20}$, most preferably $C_1$-$C_{10}$), an aryloxy group (preferably $C_6$-$C_{30}$, more preferably $C_6$-$C_{20}$, most preferably $C_6$-$C_{12}$), a heterocyclicoxy group (preferably $C_1$-$C_{30}$, more preferably $C_1$-$C_{20}$, most preferably $C_1$-$C_{12}$), an acyl group (preferably $C_1$-$C_{30}$, more preferably $C_1$-$C_{20}$, most preferably $C_1$-$C_{12}$), an alkoxycarbonyl group (preferably $C_2$-$C_{30}$, more preferably $C_2$-$C_{20}$, most preferably $C_2$-$C_{12}$), an aryloxycarbonyl group (preferably $C_7$-$C_{30}$, more preferably $C_7$-$C_{20}$, most preferably $C_7$-$C_{12}$), an acyloxy group (preferably $C_2$-$C_{30}$, more preferably $C_2$-$C_{20}$, most preferably $C_2$-$C_{10}$), an acylamino group (preferably $C_2$-$C_{30}$, more preferably $C_2$-$C_{20}$, most preferably $C_2$-$C_{10}$), an alkoxycarbonylamino group (preferably $C_2$-$C_{30}$, more preferably $C_2$-$C_{20}$, most preferably $C_2$-$C_{12}$), an aryloxycarbonylamino group (preferably $C_7$-$C_{30}$, more preferably $C_7$-$C_{20}$, most preferably $C_7$-$C_{12}$), a sulfonylamino group (preferably $C_1$-$C_{30}$, more preferably $C_1$-$C_{20}$, most preferably $C_1$-$C_{12}$), a sulfamoyl group (preferably $C_0$-$C_{30}$, more preferably $C_0$-$C_{20}$, most preferably $C_0$-$C_{12}$), a carbamoyl group (preferably $C_1$-$C_{30}$, more preferably $C_1$-$C_{20}$, most preferably $C_1$-$C_{12}$), an alkylthio group (preferably $C_1$-$C_{30}$, more preferably $C_1$-$C_{20}$, most preferably $C_1$-$C_{12}$), an arylthio group (preferably $C_6$-$C_{30}$, more preferably $C_6$-$C_{20}$, most preferably $C_6$-$C_{12}$), a heterocyclicthio group (preferably $C_1$-$C_{30}$, more preferably $C_1$-$C_{20}$, most preferably $C_1$-$C_{12}$), a sulfonyl group (preferably $C_1$-$C_{30}$, more preferably $C_1$-$C_{20}$, most preferably $C_1$-$C_{12}$), a sulfinyl group (preferably $C_1$-$C_{30}$, more preferably $C_1$-$C_{20}$, most preferably $C_1$-$C_{12}$), an ureido group (preferably $C_1$-$C_{30}$, more preferably $C_1$-$C_{20}$, most preferably $C_1$-$C_{12}$), a phophoramide group (preferably $C_1$-$C_{30}$, more preferably $C_1$-$C_{20}$, most preferably $C_1$-$C_{12}$), a hydroxyl group, a mercapto group, a halogen atom, a cyano group, a sulfo group, a carboxyl group, a nitro group, a hydroxamic group, a sulfino group, a hydrazino group, an imino group, a heterocyclic group (preferably $C_1$-$C_{30}$, more preferably $C_1$-$C_{12}$), a silyl group (preferably $C_3$-$C_{40}$, more preferably $C_3$-$C_{30}$, most preferably $C_3$-$C_{24}$) and a silyloxy group (preferably $C_3$-$C_{40}$, more preferably $C_3$-$C_{30}$, most preferably $C_3$-$C_{24}$).

The cyclometalated transition metal complex represented by the formula I may be any one of the compounds represented by Formulae II through X below:

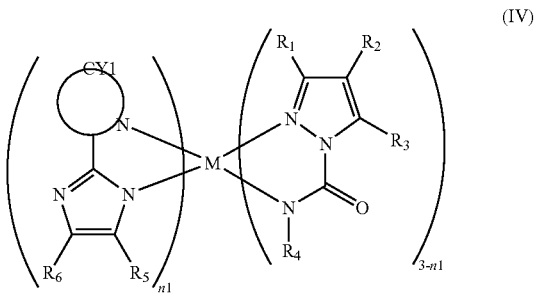

(II)

wherein each of $R_1$, $R_2$, $R_3$, $R_4$, $R_5$, $R_6$, $R_7$, $R_8$, $R_9$, $R_{10}$, $R_{11}$, and $R_{12}$ is a substituent or a hydrogen atom;
M is a transition metal; and
n1 is 1 or 2.

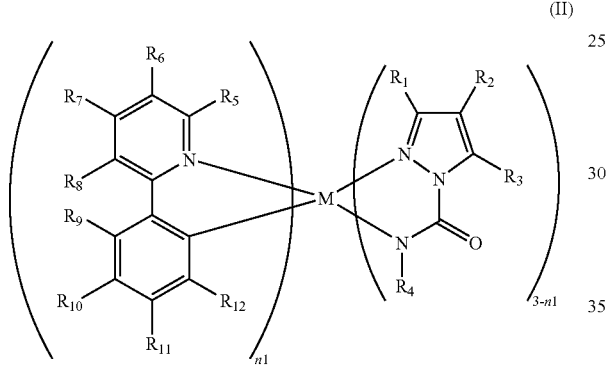

(III)

wherein each of $R_1$, $R_2$, $R_3$, $R_4$, $R_5$, and $R_6$ is a substituent or a hydrogen atom;
M is a transition metal;
n1 is 1 or 2; and
CY1 is an aromatic ring or an aliphatic ring.

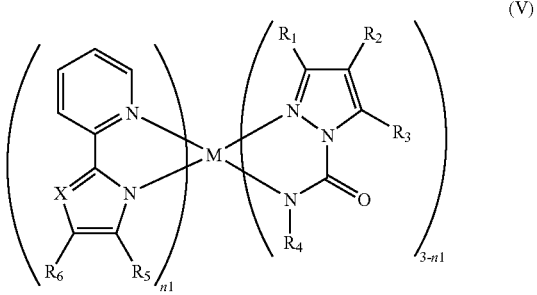

(IV)

wherein each of $R_1$, $R_2$, $R_3$, $R_4$, $R_5$, and $R_6$ is a substituent or a hydrogen atom;
M is a transition metal;
n1 is 1 or 2; and
CY1 is an aromatic ring or an aliphatic ring.

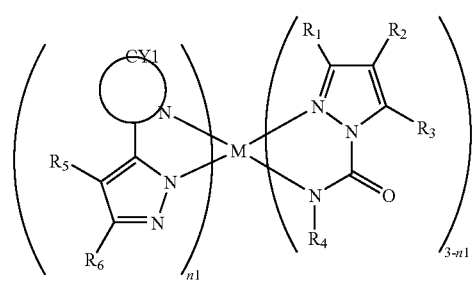

(V)

wherein each of $R_1$, $R_2$, $R_3$, $R_4$, $R_5$, and $R_6$ is a substituent or a hydrogen atom;
M is a transition metal;
X is C, N, O, S or P; and
n1 is 1 or 2.

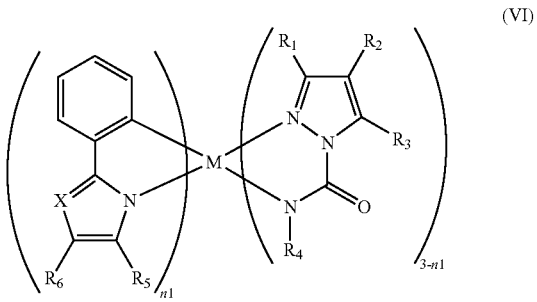

(VI)

wherein each of $R_1$, $R_2$, $R_3$, $R_4$, $R_5$, and $R_6$ is a substituent or a hydrogen atom;

M is a transition metal;
X is C, N, O, S or P; and
n1 is 1 or 2.

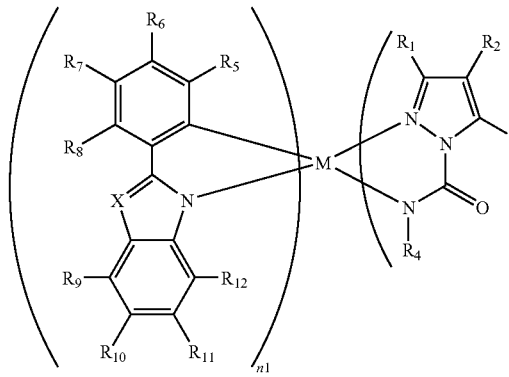

(VII)

wherein each of $R_1, R_2, R_3, R_4, R_5, R_6, R_7, R_8, R_9, R_{10}, R_{11}$, and $R_{12}$ is a substituent or a hydrogen atom;
M is a transition metal;
X is C, N, O, S or P; and
n1 is 1 or 2.

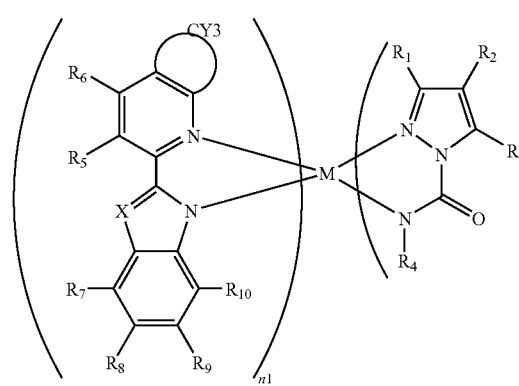

(VIII)

wherein each of $R_1, R_2, R_3, R_4, R_5, R_6, R_7, R_8, R_9$, and $R_{10}$ is a substituent or a hydrogen atom;
M is a transition metal;
X is C, N, O, S or P;
CY3 is an aromatic ring or an aliphatic ring; and
n1 is 1 or 2.

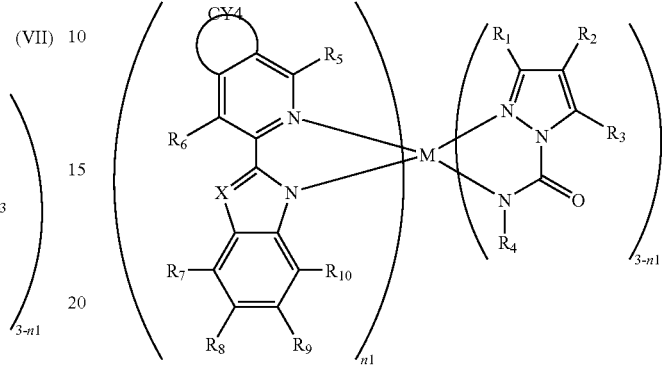

(IX)

wherein each of $R_1, R_2, R_3, R_4, R_5, R_6, R_7, R_8, R_9$, and $R_{10}$ is a substituent or a hydrogen atom;
M is a transition metal;
X is C, N, O, S or P;
CY4 is an aromatic ring or an aliphatic ring, and
n1 is 1 or 2.

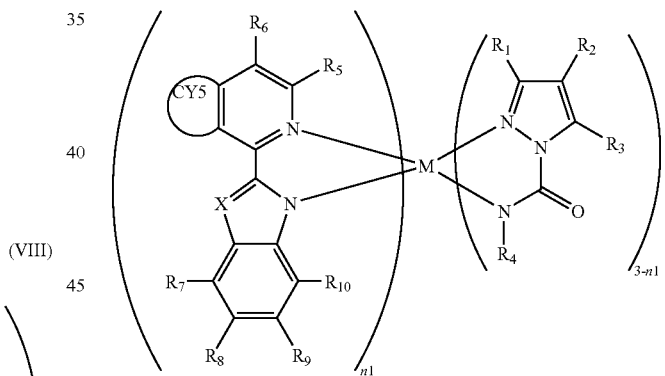

(X)

wherein each of $R_1, R_2, R_3, R_4, R_5, R_6, R_7, R_8, R_9$, and $R_{10}$ is a substituent or a hydrogen atom;
M is a transition metal;
X is C, N, O, S or P;
CY5 is an aromatic ring or an aliphatic ring; and
n1 is 1 or 2.

In the formulae II through X, $R_1, R_2, R_3, R_4, R_5, R_6, R_7, R_8, R_9, R_{10}, R_{11}$, and $R_{12}$ may include the substituents defined in $R_1, R_2, R_3$, and $R_4$ of the formula I.

In the formulae I through X, CY1, CY2, CY3, CY4 and CY5 may include aromatic hydrocarbon rings such as a benzene ring, a naphthalene ring, a quinoxaline and an anthracene ring; aromatic heterocycles such as a pyridine ring, a pyrazine ring, a quinoline ring, a furan ring and a thiophene ring; aliphatic hydrocarbon rings such as a cyclohexane ring; and aliphatic heterocycles such as a pyrane ring.

In the formula I, the transition metal M may be Ru, Rh, Os, Ir, Pt or Au.

The cyclometalated transition metal complex may be any one of the compounds represented by the formulae below, however, is not limited to these:

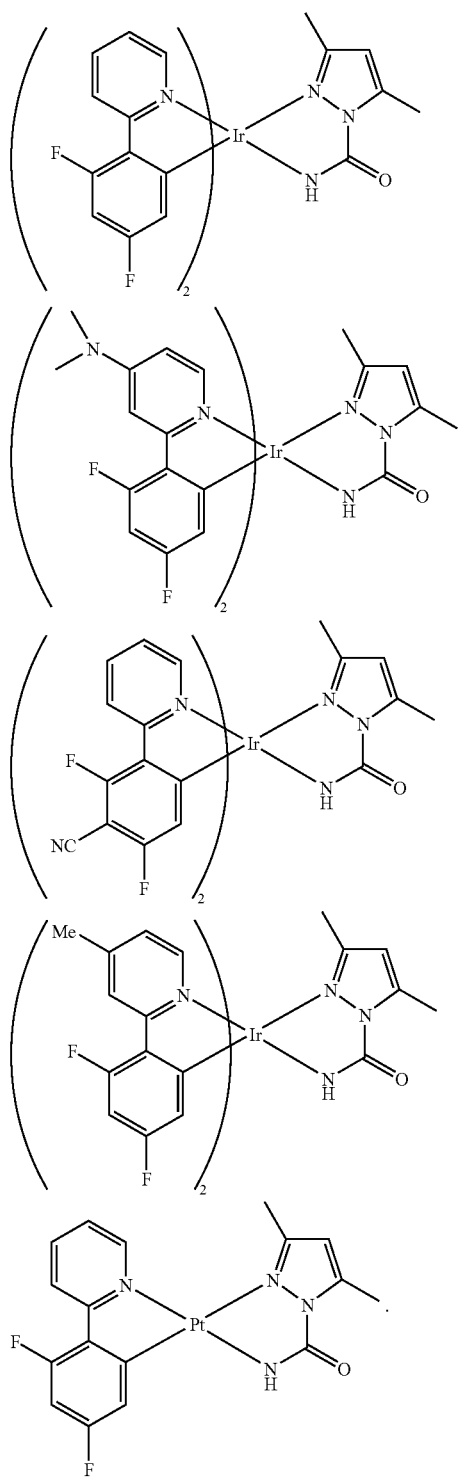

The transition metal complex according to the present invention has light-emitting property at a wavelength range of 400 nm to 680 nm.

The transition metal complex according to the present invention can be synthesized by using the starting material $[Ir(C^\wedge N)_2Cl]_2$ derivative that provides a cyclometalated moiety according to the method reported by Watts and his colleagues (F. O. Garces, R. J. Watts, Inorg. Chem. 1988, (35), 2450, which is incorporated herein by reference).

Hereinafter, the synthetic method will be described concerning the synthetic pathways of an iridium complex according to an embodiment of the present invention.

Referring the reaction scheme I below, a cyclometalated transition metal complex can be synthesized by mixing the starting material $[Ir(C^\wedge N)_2Cl]_2$ derivative and a pyrazolecarboxamide compound with a solvent such as a chloroform and a methanol, and stirring the resulting mixture for 2 to 48 hours at room temperature:

Reaction scheme I

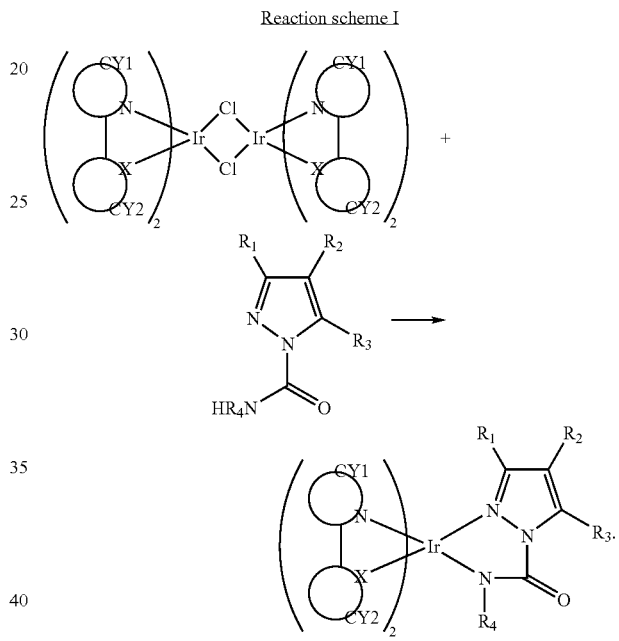

In the reaction scheme I, X, $R_1$, $R_2$, $R_3$, $R_4$, CY1 and CY2 are the same as defined in the formula I.

The organic electroluminescent device according to the present invention is prepared by forming an organic film, particularly a light emitting layer employing the cyclometalated transition metal complex according to the present invention. The transition metal complex represented by the formula I is very useful as a phosphorescent dopant material that is a light emitting layer-forming material, and provides excellent light-emitting properties in the range of blue wavelengths.

When the transition metal complex according to the present invention is used as a phosphorescent dopant, an organic film may further comprise at least one selected from the group consisting of at least one of polymer hosts, a mixed host of a polymer and a low molecular weight compound, a low molecular weight host, and a non-luminescent polymer matrix. Herein, any materials that are typically used for forming a light-emitting layer for an organic electroluminescent device can be used as the polymer host, the low molecular weight host and a non-luminescent polymer matrix. The polymer host includes a polyvinylcarbazole (PVK) and a polyfluorene, and the low molecular weight host includes a 4,4'-N,N'-dicarbazole-biphenyl (CBP), a 4,4'-bis[9-(3,6-biphenylcarbazolyl)]-1,1'-biphenyl, a 9,10-bis[(2',7'-t- butyl)-9',9"-spiro bifluorenyl anthracene, and a tetrafluorene and the like. The non-luminescent polymer matrix includes a polymethylmethacrylate and a polystyrene, etc., however, is not limited to these.

The amount of the transition metal complex according to the present invention may be 1 to 30 parts by weight, based on 100 parts by weight of the total weights of the light-emitting layer-forming material. The incorporation of the transition metal complex into the light-emitting layer can be carried out by vacuum vapor deposition, sputtering, printing, coating, ink jetting, or a method using electronic beam, etc.

Further, the transition metal complex according to the present invention can emit white light by using a green light-emitting material or a red light-emitting material together.

The thickness of the organic film may be 30 nm to 100 nm. The organic film used herein refers to a film of an organic compound, which is formed between a pair of electrodes in an organic electroluminescent display device, such as an electron transporting layer and a hole transporting layer, in addition to a light emitting layer. Such an organic electroluminescent display device can have commonly known various structures, such as anode/light emitting layer/cathode, anode/buffer layer/light emitting layer/cathode, anode/hole transporting layer/light emitting layer/cathode, anode/buffer layer/hole transporting layer/light emitting layer/cathode, anode/buffer layer/hole transporting layer/light emitting layer/electron transporting layer/cathode, anode/buffer layer/hole transporting layer/light emitting layer/hole blocking layer/cathode and the like, but the structures are not limited to these.

The buffer layer may be composed of a material commonly used for a buffer, and may be composed of, but is not limited to, a copper phthalocyanine, a polythiophene, a polyaniline, a polyacetylene, a polypyrrole, a polyphenylene vinylene or their derivatives.

The hole transporting layer may be composed of a material commonly used for a hole transporting layer, and may be composed of, but is not limited to, a polytriphenylamine.

The electron transporting layer may be composed of a material commonly used for an electron transporting layer, and may be composed of, but is not limited to, a polyoxadiazole.

The hole blocking layer may be composed of a material commonly used for a hole blocking layer, and may be composed of, but is not limited to, LiF, $BaF_2$ or $MgF_2$ and the like.

The organic electroluminescent display device according to the present invention may be prepared by a common method of manufacturing an organic electroluminescent display device employing common luminescent materials, and thus does not need any special apparatuses or processes.

The cyclometalated transition metal complex can emit light at a wavelength range of 400 nm to 680 nm. The light emitting diode employing such an organic metal complex may be used in light source illumination for displaying full color, backlight, an outdoor bulletin board, optical communication, and interior decoration, etc.

Hereinafter, the present invention will be described in greater detail with reference to the following examples. The following examples are for illustrative purposes and are not intended to limit the scope of the invention.

EXAMPLES

Reference Example 1

Synthesis of $[(F_2ppy)_2IrCl]_2$ ($F_2ppy$ dimer)

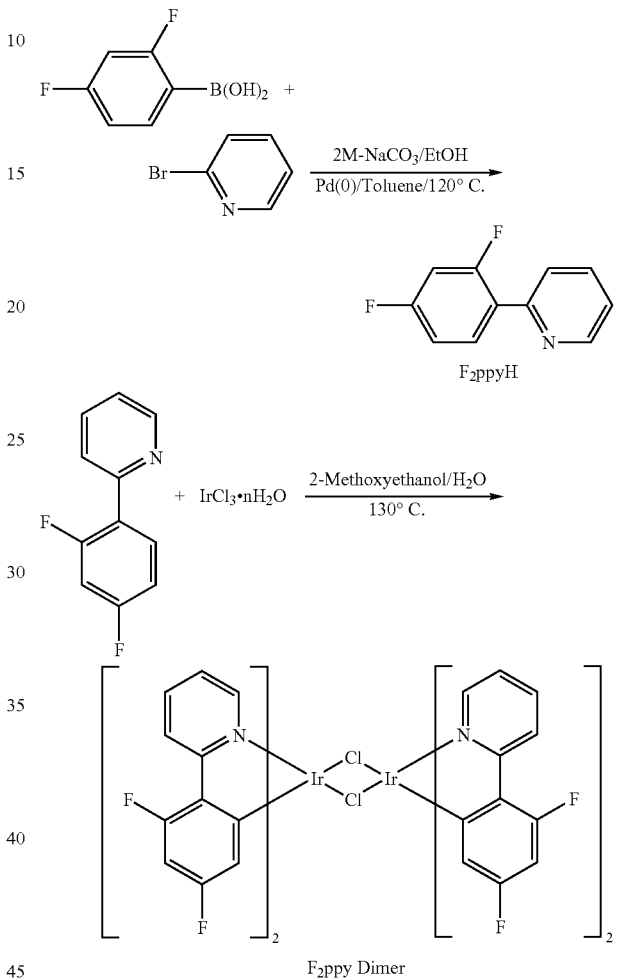

$F_2ppy$ Dimer

To a 500 ml flask with a side arm, 19.85 g (125 mmol) of 2-bromopyridine, 25.00 g (158 mmol) of a 2,4-difluorophenyl boronic acid), 100 ml of a toluene, 48 ml of an ethanol and 2M sodium carbonate solution in 95 ml of water were added, and the mixture was agitated under nitrogen atmosphere at room temperature. Then, 4.53 g (3.92 mmol) of a tetrakis (triphenylphosphine) palladium(0) were added to the reaction mixture, and the mixture was refluxed under the nitrogen atmosphere for 15 hrs in a dark room.

After the temperature of the reaction mixture was returned to room temperature on completion of the reaction, an organic layer was extracted using ethyl acetate and water. Then, the extract was separated by column chromatography (toluene:hexane=10:1) to obtain a pale brown liquid ($F_2ppyH$).

$^1$H-NMR($CD_2Cl_2$, ppm): 8.69 (d, 1H), 8.03 (m, 1H), 7.70 (m, 2H), 7.27 (m, 1H), 7.00 (m, 2H).

A yellow powder of $[(F_2ppy)_2IrCl]_2$ dimer was synthesized by using 2-(4,6-difluorophenylpyridine) monomer synthesized according to the above procedure and $IrCl_3 \cdot nH_2O$.

Herein, the synthesis was performed with reference to J. Am. Che. Soc., 1984, 106, 6647-6653, which is incorporated herein by reference.

$^1$H-NMR(CD$_2$Cl$_2$, ppm): 9.1 (d, 4H), 8.3 (d, 4H), 7.9 (t, 4H), 6.9 (m, 4H), 6.5 (m, 4H), 5.3 (d, 4H).

Reference Example 2

Synthesis of [(MeF$_2$ppy)$_2$IrCl]$_2$

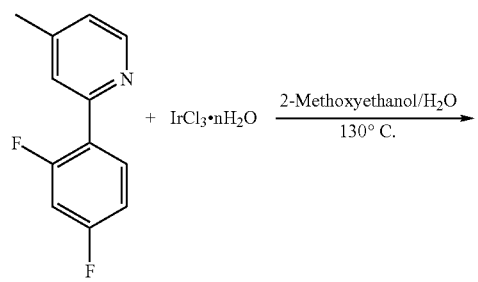

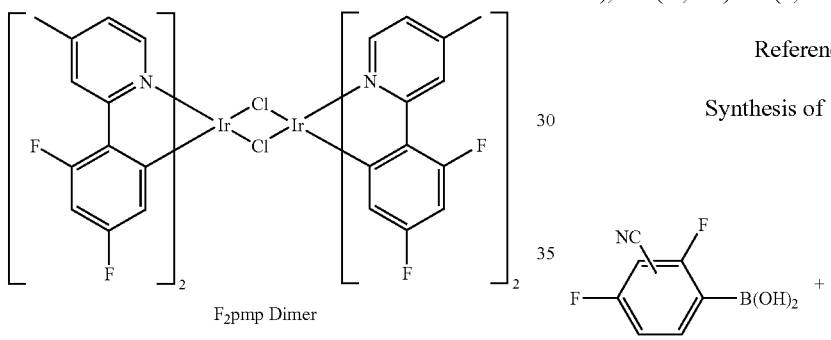

F$_2$pmp Dimer

A [(MeF$_2$ppy)$_2$IrCl]$_2$ (F$_2$pmp dimer) was synthesized by using the same method as in the reference example 1, except that a 2-bromo-4-methylpyridine was used instead of a 2-bromopyridine.

$^1$H-NMR(CD$_2$Cl$_2$, ppm): 8.9 (d, 4H), 8.1 (s, 4H), 6.6 (d, 4H), 6.3 (m, 4H), 5.3 (d, 4H), 2.6 (s, 12H).

Reference Example 3

Synthesis of [(DMAF$_2$ppy)$_2$IrCl]$_2$

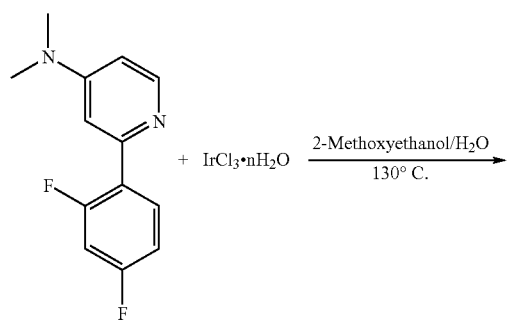

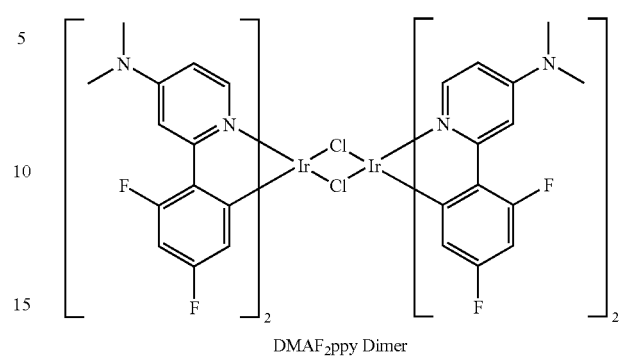

DMAF$_2$ppy Dimer

A [(DMAF$_2$ppy)$_2$IrCl]$_2$ (DMAF$_2$ppy dimer) was synthesized by using the same method as in the reference example 1, except that 25.26 g (1.25×10$^4$ mmol) of a 2-bromo-4-dimethylaminopyridine were used instead of a 2-bromopyridine.

$^1$H-NMR(CD$_2$Cl$_2$, ppm): 8.7 (d, 4H), 7.5 (t, 4H), 6.3 (m, 4H), 6.1 (m, 4H) 5.4 (d, 4H), 3.2 (s, 24H).

Reference Example 4

Synthesis of [(F$_2$CNppy)$_2$IrCl]$_2$

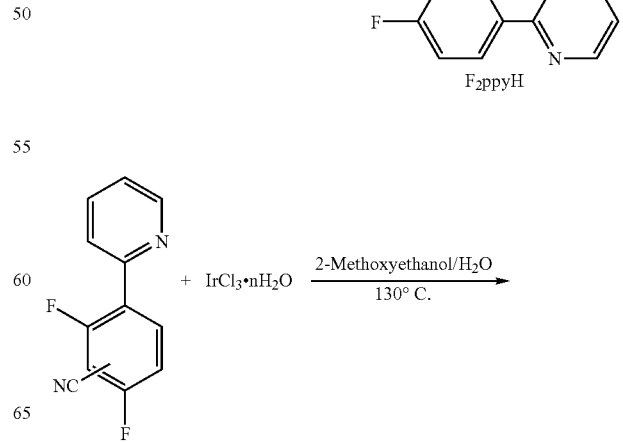

-continued

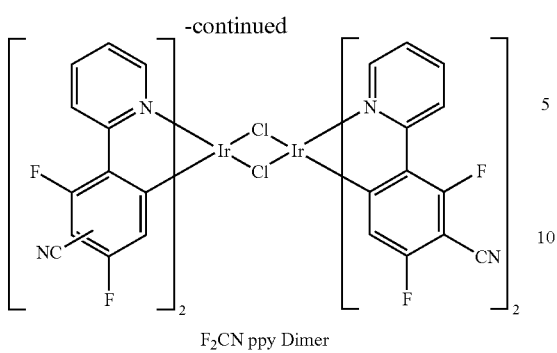

F₂CN ppy Dimer

An [(F₂CNppy)₂IrCl]₂ (F₂CNppy dimer) was synthesized by using the same method as in the reference example 1, except that 22.87 g (125 mmol) of a 2,4-difluoro-3-cyanophenylboronic acid were used instead of a 2,4-difluorophenylboronic acid.

Reference Example 5

Synthesis of [(F₂ppy)PtCl]₂ (F₂ppy dimer)

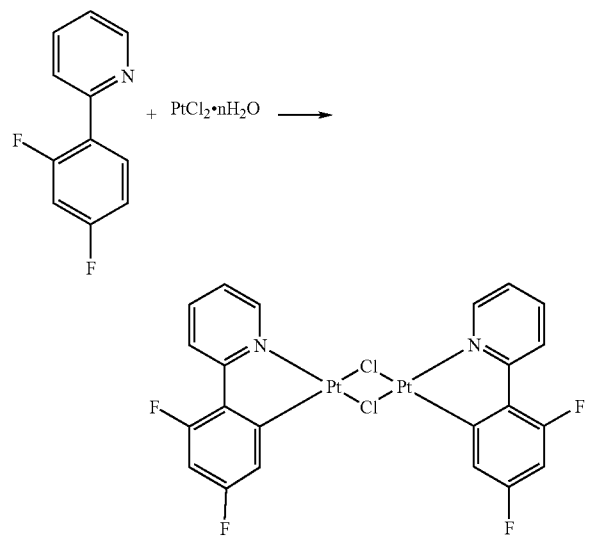

To a 500 ml flask with a side arm, 19.85 g (1.25×10⁴ mmol) of 2-bromopyridine, 25.00 g (1.58×10⁴ mmol) of a 2,4-difluorophenyl boronic acid), 100 ml of a toluene, 48 ml of an ethanol and 2M sodium carbonate solution in of water were added, and the mixture was agitated under nitrogen atmosphere at room temperature. Then, 4.53 g (3.92 mmol) of a tetrakis(triphenylphosphine) palladium(0) were added to the reaction mixture, and the mixture was refluxed under the nitrogen atmosphere for 15 hrs in a dark room.

After the temperature of the reaction mixture was returned to room temperature on completion of the reaction, an organic layer was extracted using ethyl acetate and water. Then, the extract was separated by column chromatography (toluene:hexane=10:1) to obtain a pale brown liquid (F₂ppyH).

¹H-NMR(CD₂Cl₂, ppm): 8.69 (d, 1H), 8.03 (m, 1H), 7.70 (m, 2H), 7.27 (m, 1H), 7.00 (m, 2H).

A green powder [(F₂ppy)PtCl]₂ dimer was synthesized by using 2-(4,6-difluorophenylpyridine) monomer synthesized according to the above procedure and K₂[PtCl]₄. Herein, the synthesis was performed with reference to J. Am. Che. Soc., 1984, 106, 6647-6653.

Example 1

Preparation of Compound (1) (F₂PZNH)

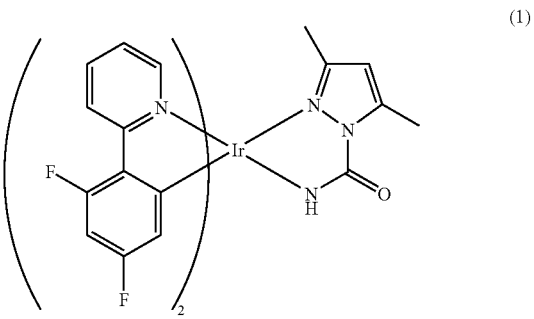

(1)

In the 100 ml 2-neck flask equipped with a thermometer, a mechanical stirrer and a reflux condenser, 0.605 g (0.5 mmol) of [(F₂ppy)₂IrCl]₂ prepared in the reference example 1 and 0.160 g (1.25 mmol) of 3,5-dimethylpyrazole-1-carboxamide were dissolved in 30 ml of a mixed solution of methanol and chloroform under nitrogen atmosphere, and the resulting solution was stirred for about 2 hrs at room temperature. Then, the reaction temperature was slowly elevated and the reaction mixture was refluxed for 8 hours. After completion of the reaction, the reaction mixture was cooled to room temperature, and then unreacted starting materials were removed by filtering. The solvents were all removed from the filtrate with a rotatory evaporator, and diethyl ether was added in droplets. The resulting green solid was filtered with a filter paper, and washed several times with diethyl ether and hexane. Yellow solid was fully dried in a vacuum oven at 30° C., and was weighed. 0.55 g (yield: 87%) of the title compound were obtained as pure green solid, and the melting point of the compound was 255° C. The synthesized compound was confirmed by ¹H NMR and MS (FIG. 1).

Example 2

Preparation of Compound (2) (MeF₂PZNH)

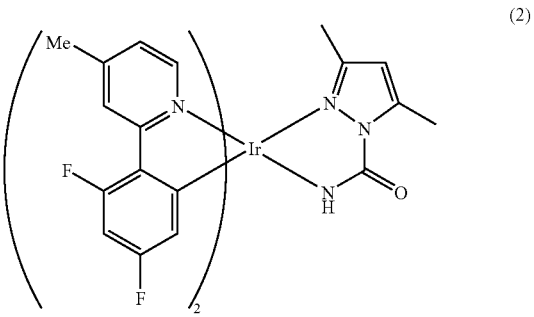

(2)

0.575 g (yield: 85%) of the title compound were obtained as pure pale green solid by performing the same method as in the example 1, except that 0.65 g (0.5 mmol) of [(MeF₂ppy)

$_2$IrCl]$_2$ prepared in the reference example 2 were used instead of [(F$_2$ppy)$_2$IrCl]$_2$. The melting point of the compound was 260° C. The synthesized compound was confirmed by $^1$H NMR and MS.

Example 3

Preparation of Compound (3) (DMAF$_2$PZNH)

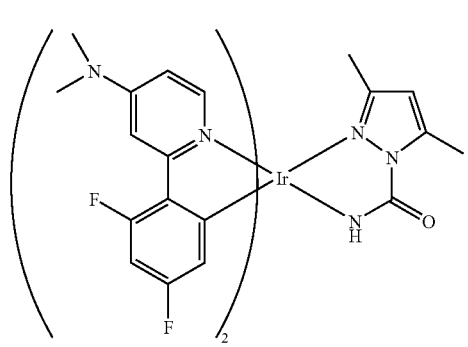

(3)

0.63 g (yield: 85%) of the title compound were obtained as pure pale green solid by performing the same method as in the example 1, except that 0.71 g (0.5 mmol) of [(DMAF$_2$ppy)$_2$IrCl]$_2$ prepared in the reference example 3 were used instead of [(F$_2$ppy)$_2$IrCl]$_2$. The melting point of the compound was 255° C. The synthesized compound was confirmed by $^1$H NMR and MS (FIG. 1).

Example 4

Preparation of Compound (4) (F$_2$CNPZNH)

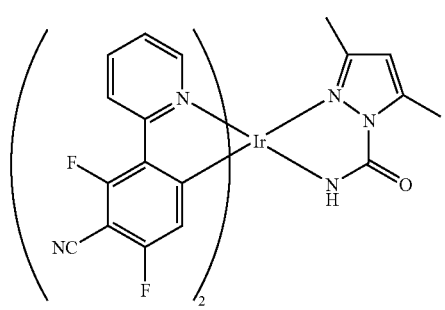

(4)

0.580 g (yield: 83%) of the title compound were obtained as pale green solid by performing the same method as in the example 1, except that 0.67 g (0.5 mmol) of [(F$_2$CNppy)$_2$IrCl]$_2$ prepared in the reference example 4 were used instead of [(F$_2$ppy)$_2$IrCl]$_2$.

The synthesized compound was confirmed by $^1$H NMR and MS (FIG. 1).

Example 5

Preparation of Compound (5) (F$_2$PZNH(Pt))

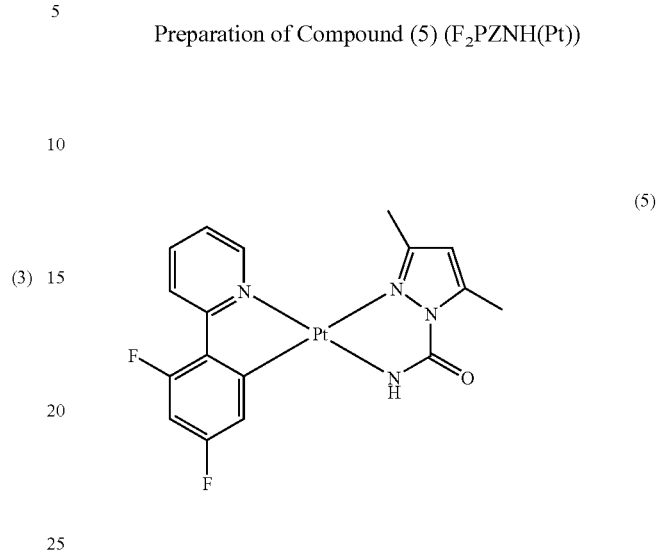

(5)

0.690 g (yield: 80%) of the title compound were obtained by performing the same method as in the example 1, except that 0.84 g (1 mmol) of [(F$_2$ppy)PtCl]$_2$ prepared in the reference example 5 were used instead of [(F$_2$ppy)$_2$IrCl]$_2$. The synthesized compound was confirmed by $^1$H NMR and MS.

The light emitting characteristics for the compounds obtained from the above procedure were examined according to the methods below.

In the first method, the compound was dissolved in methylene chloride to prepare $10^{-4}$ M solution, and then the light emitting characteristics in the state of a methylene chloride solution were examined. In the second method, 94 parts by weight of polymethylmethacrylate (PMMA) and 6 parts by weight of the compound were dissolved in a solvent, the solution was spin coated to prepare a film, and the light emitting characteristics in the film state were examined. The maximum light emitting wavelength, the color coordinate (CIE), the degradation temperature and HOMO level for the compounds obtained from the examples were summarized in Table 1 below.

TABLE 1

| Compound No. | $\lambda_{max}$ (nm, solution) | $\lambda_{max}$ (nm, film) | Color coordinate (x, y) | Degradation temperature (° C.) | HOMO |
|---|---|---|---|---|---|
| 1 | 474 | 473 | 0.15, 0.31 | 255 | 5.68 |
| 2 | 469 | 469 | 0.15, 0.27 | 260 | |
| 3 | 474 | 472 | 0.15, 0.25 | 255 | |
| 4 | 465 | 464 | 0.14, 0.24 | | 5.92 |
| 5 | 469, 494 | 469, 494, 531, 612 | 0.33, 0.38 (film) | | |

Figure 6:
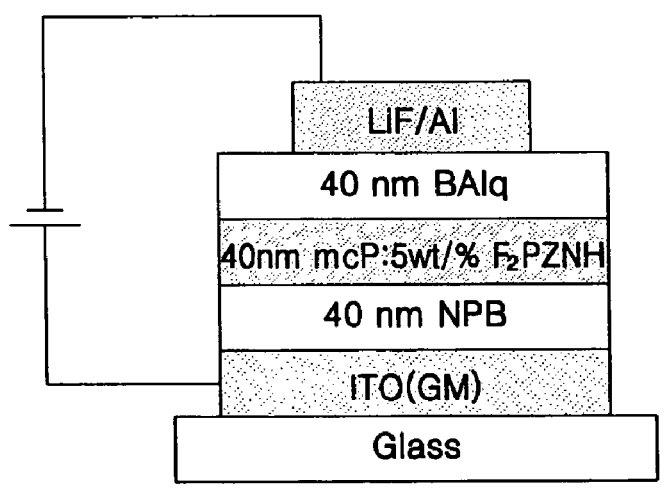
FIG. 6 is a schematic diagram showing the structure of an organic electroluminescent display device employing the compounds according to the example 1 of the present invention.

The EL display device adopting the compound synthesized in the examples had the following multilayer structure (refer to FIG. 6), and its light emitting area was 9 mm$^2$:

substrate/first electrode/hole transporting layer/light emitting layer/hole blocking layer/electron transporting layer/electron injecting layer/second electrode=
glass/ITO/NBP(40 nm)/mCP:5 wt % F$_2$PZNH(40 nm)/BAlq(40 nm)/LiF(2 nm)/Al(200 nm).

The display device was manufactured as follows.

After NPB was deposited on the pre-washed ITO with a thickness of 40 nm, F$_2$PZNH was mixed with a host mCP (N,N'-dicarbazolyl-3,5-benzene) (in a ratio of 95:5 (wt %) and coated on the deposits. BAlq was coated onto this as a positive charge blocking layer (hole blocking layer (HBL)) with a thickness of 40 nm by heat depositing method, LiF was coated onto this as a negative charge transporting layer (electron transporting layer (ETL)) with a thickness of 2 nm, and finally Al was coated as an anode with a thickness of 200 nm.

The evaluation results for the device (maximum light emitting wavelength, color coordinate, brightness, lifetime, etc.) are summarized in Table 2.

TABLE 2

| $\lambda_{max}$ (nm, PL) | CIE PL | $\lambda_{max}$ (nm, EL) | CIE EL | $\eta_A$ Cd/A | $\eta_{ex}$ % | Maximum brightness (Cd/m$^2$) | lifetime (hr) (2.5 mA/cm$^2$) |
|---|---|---|---|---|---|---|---|
| 474 | 0.15, 0.31 | 474, 499 | 0.18, 0.38 | 6.5 | 3.1 | 17030 | 34.1 |

Figure 2:
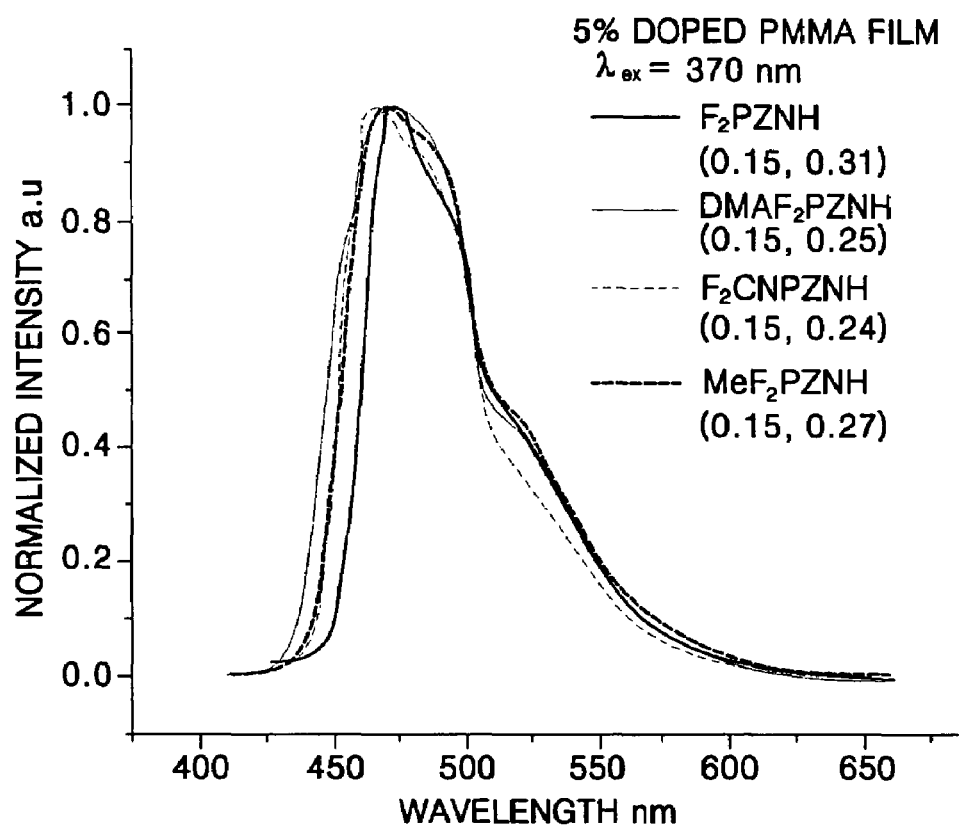
FIG. 2 is a PL (photoluminescence) spectrum of the compounds according to the examples 1 to 4 of the present invention.
Figure 3:
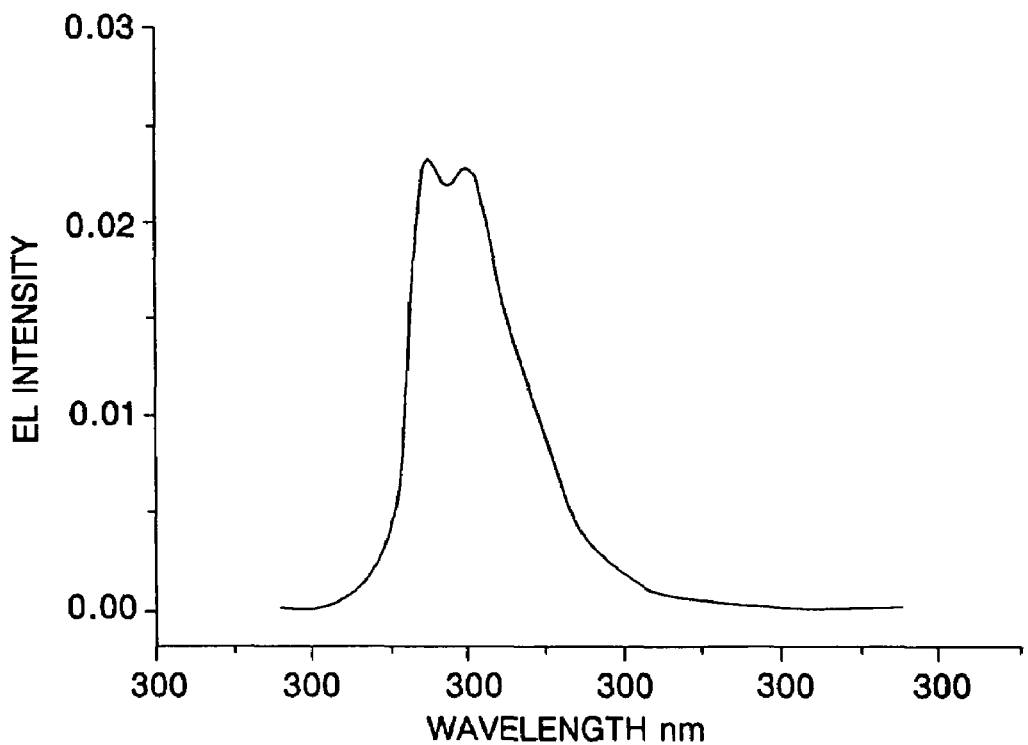
FIG. 3 is an EL (electroluminescence) spectrum of the compound according to the example 1 of the present invention.

FIG. 1 shows a mass spectrum of the compounds according to the examples 1 and 3 of the present invention, FIG. 2 is a PL (photoluminescence) spectrum of the compounds according to the examples 1 to 4 of the present invention, and FIG. 3 shows an electroluminescence (EL) intensity of the compound according to the example 1 of the present invention.

Figure 4:
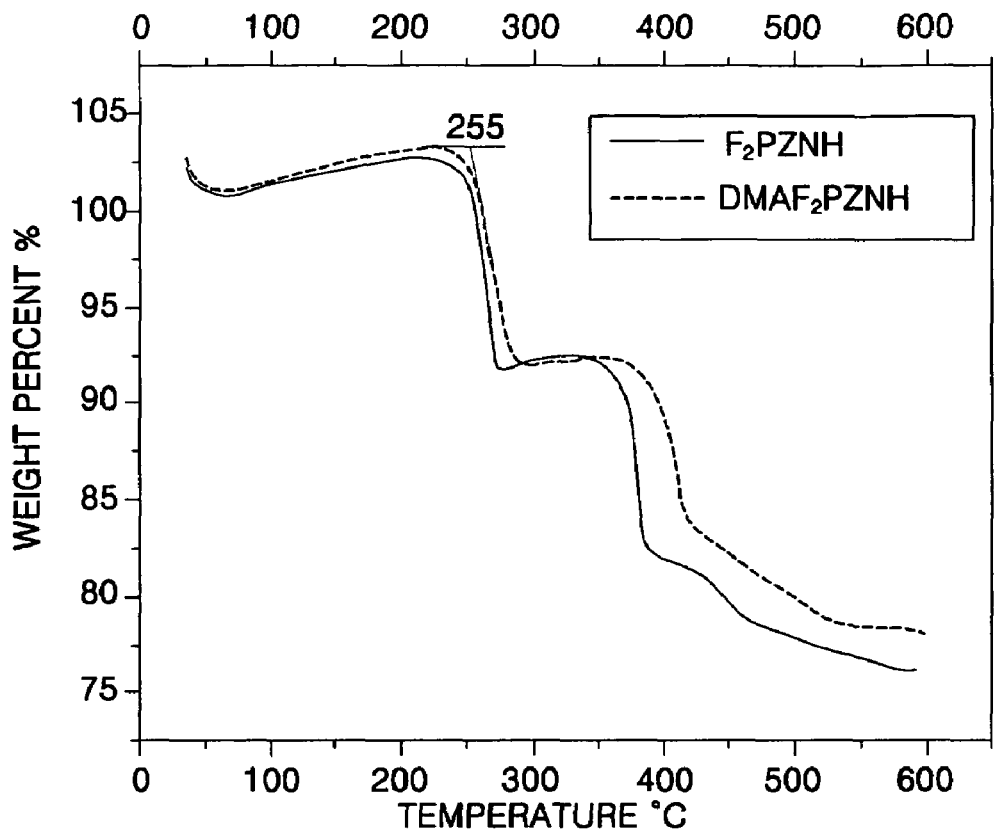
FIG. 4 is a TGA (thermo-gravimetric analyzer) graph of the compounds according to the examples 1 and 3 of the present invention.

FIG. 4 is a TGA (thermo-gravimetric analyzer) graph of the compounds according to the examples 1 and 3 of the present invention.

Figure 5A:
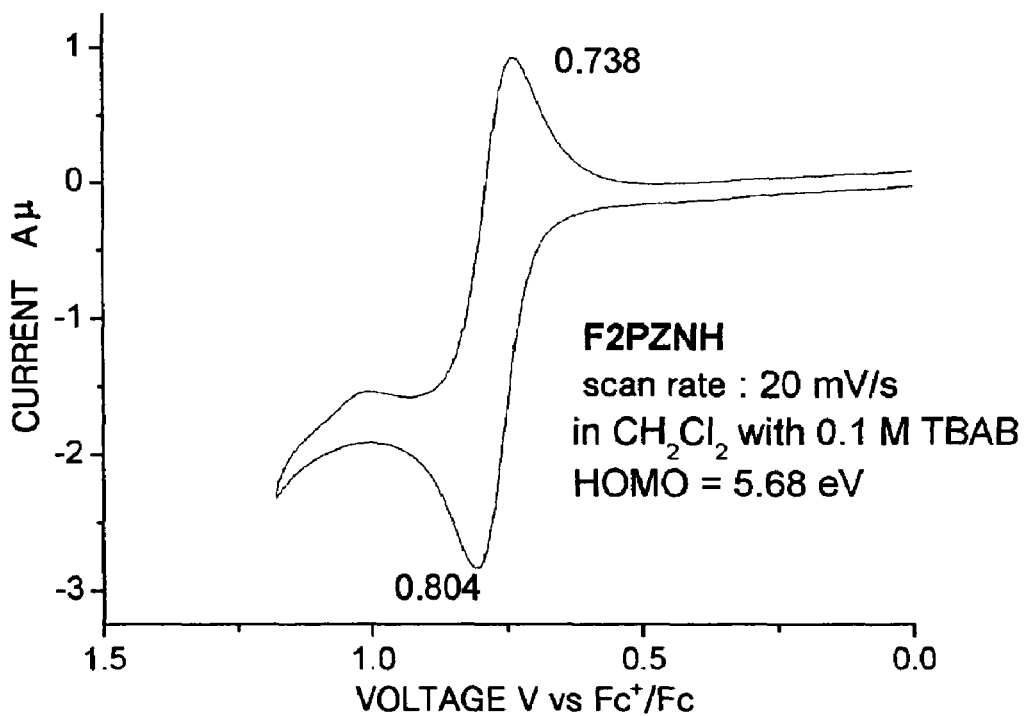
FIGS. 5A and 5B are graphs showing the oxidative cyclovoltamogram of the compounds according to the examples 1 and 4 of the present invention.
Figure 5B:
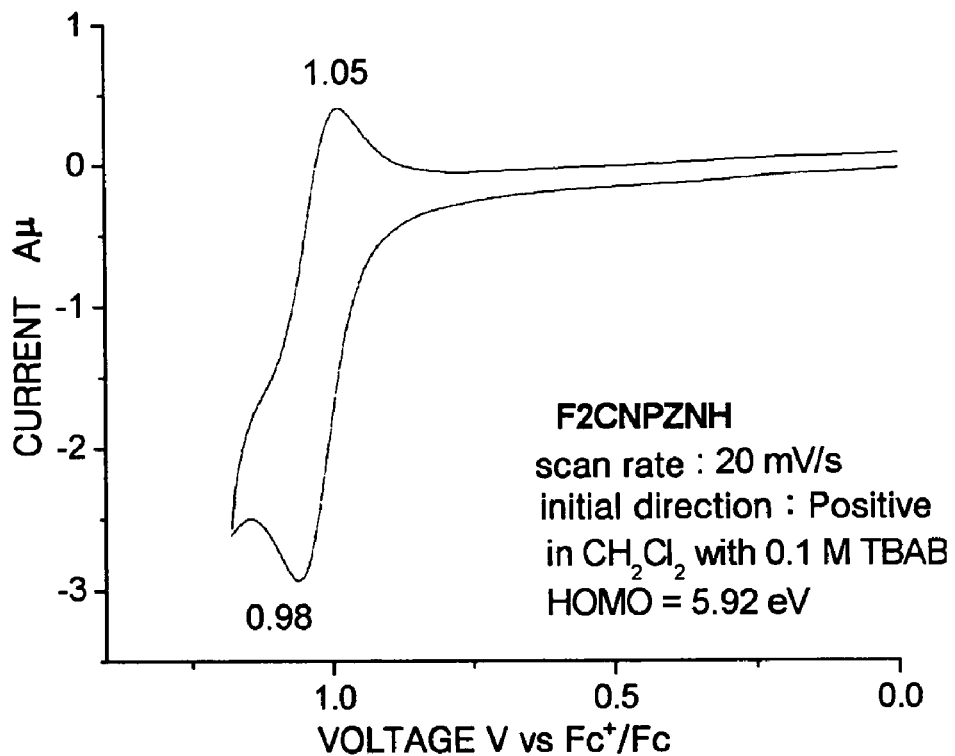

FIGS. 5A and 5B are graphs showing the oxidative cyclovoltammogram of the compounds according to the examples 1 and 4 of the present invention. From the figure, the HOMO level can be seen, and accordingly it can be seen that the compounds have semi-reversibility.

Figure 7:
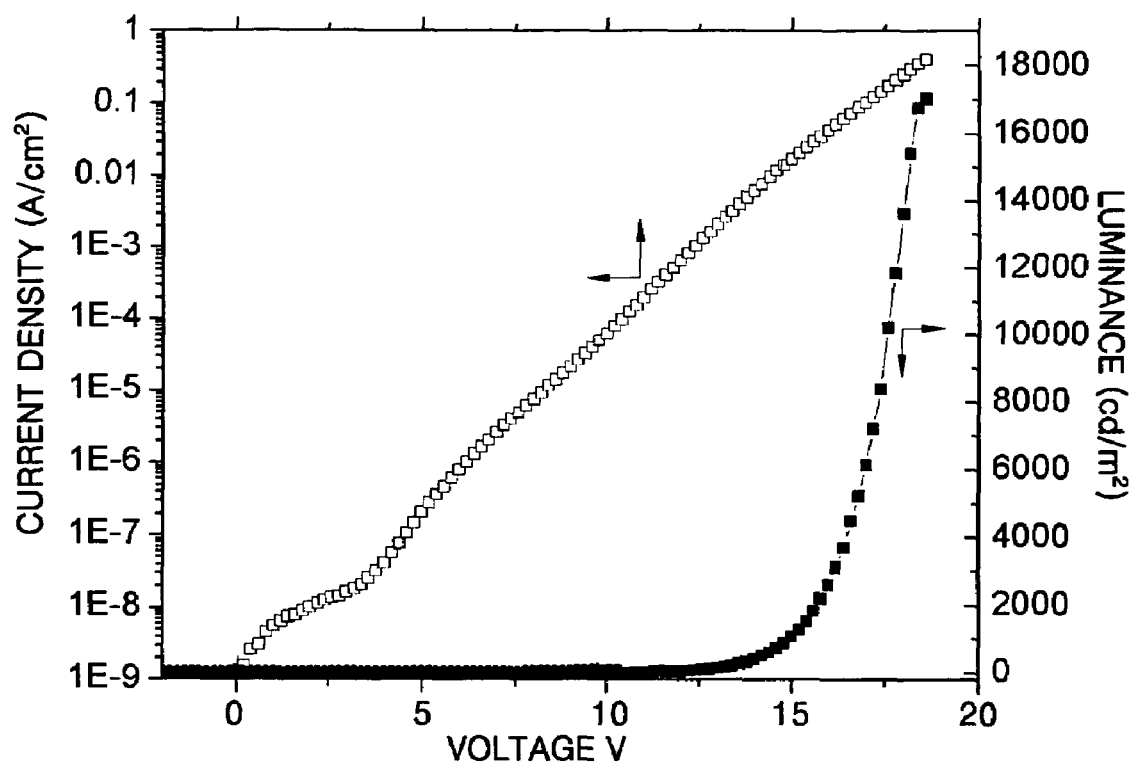
FIG. 7 is a graph showing the I-V-L property of an organic electroluminescent display device employing the compounds according to the example 1 of the present invention.

FIG. 7 is a graph showing the I-V-L property of an organic electroluminescent display device employing the compounds according to the example 1 of the present invention. From the figure, it can be seen that the turn-on voltage is low.

Figure 8:
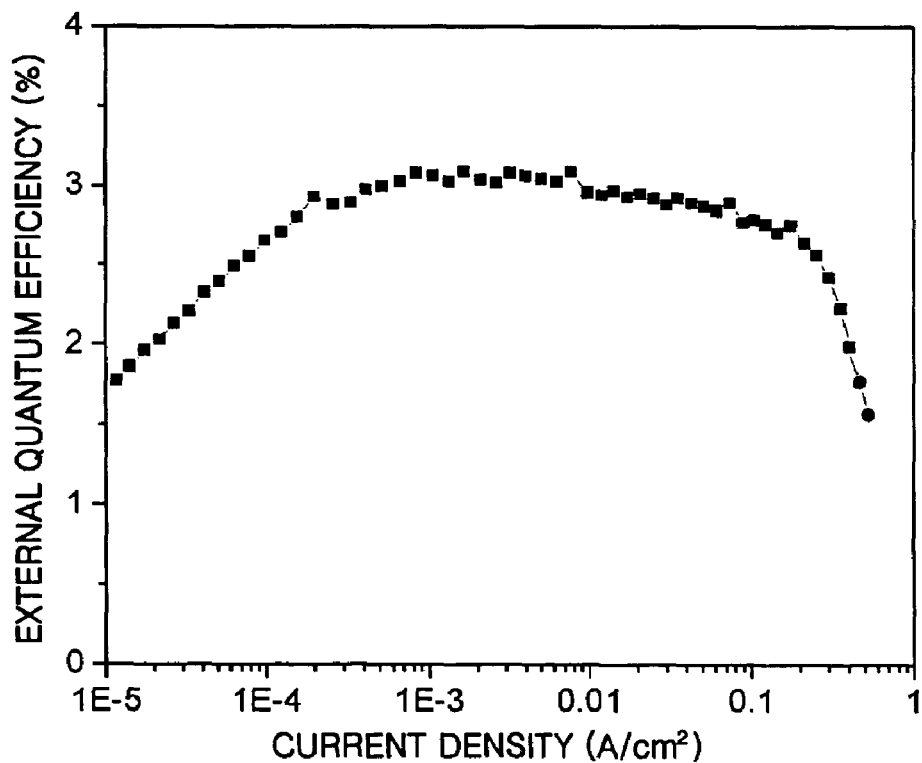
FIG. 8 is a graph showing the external quantum efficiency of an organic electroluminescent display device employing the compounds according to the example 1 of the present invention.
Figure 9:
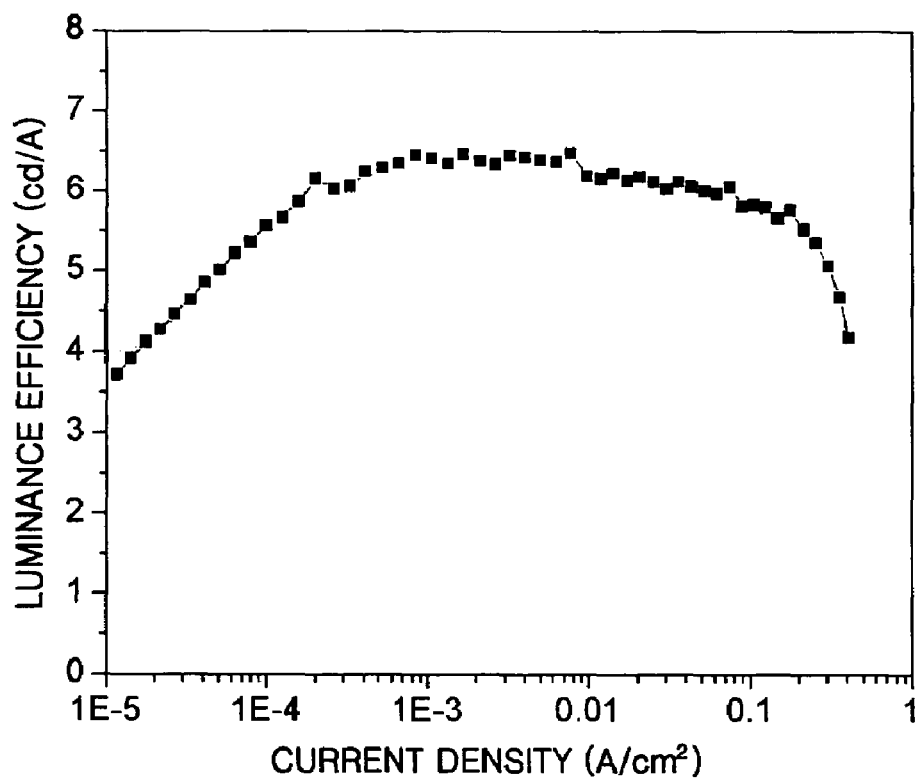
FIG. 9 is a graph showing the luminance efficiency of an organic electroluminescent display device employing the compounds according to the example 1 of the present invention.
Figure 10:
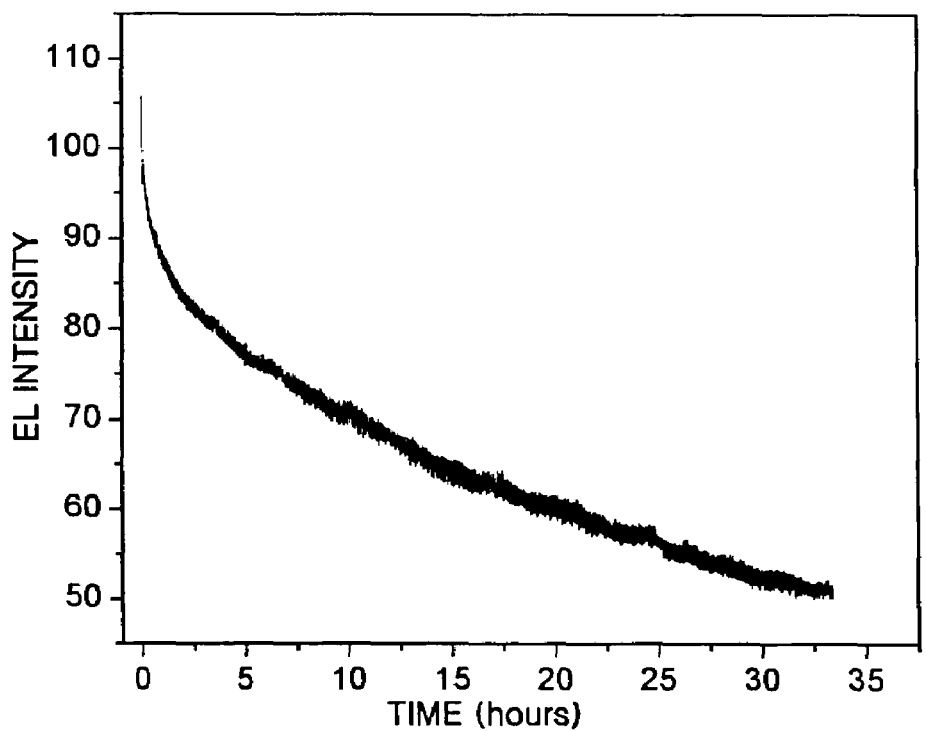
FIG. 10 is a graph showing the lifetime of an organic electroluminescent display device at 2.5 mA/cm$^2$ employing the compounds according to the example 1 of the present invention.

FIGS. 8 through 10 are graphs showing the external quantum efficiency, the luminance efficiency and lifetime (2.5 mA/cm$^2$) of the display device employing compounds according to the example 1 of the present invention.

From the foregoing, it can be seen that on incorporation of a pyrazolecarboxamide ligand, a dopant having excellent phosphorescent property is formed and is suitable as a blue phosphorescent material. Further, it can be seen that the full color of red, green and blue is embodied by incorporating various main ligands.

A cyclometalated transition metal complex according to the present invention can emit light at a wavelength range from the blue region to the red region more efficiently by triplet metal-to-ligand charge-transfer (MLCT). This organic metal complex can be used in forming an organic film of an organic electroluminescent display device. The organic metal complex can emit light at the wavelength range of 400 to 650 nm as a phosphorescent material with high efficiency. Further, the complex can emit white light by using a green light emitting material or a red light emitting material together.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A transition metal complex represented by Formula I or Formula XI:

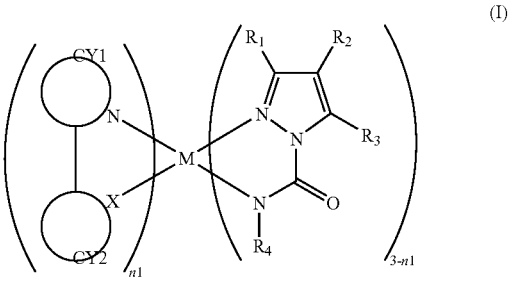

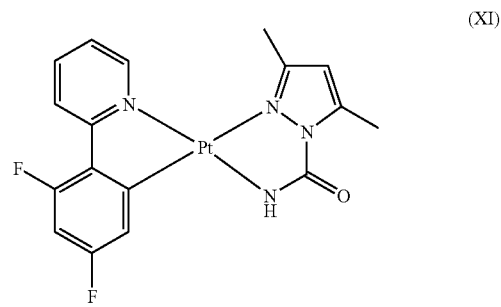

wherein M is a transition metal;

each of R$_1$, R$_2$, R$_3$ and R$_4$ is a substituent or a hydrogen atom;

X is N or C;

each of CY1 and CY2 is an aromatic ring or an aliphatic ring, and n1 is 1 or 2.

2. The transition metal complex according to claim 1, wherein R$_1$, R$_2$, R$_3$ and R$_4$ are independently a hydrogen atom, or a substituent selected from the group consisting of an alkyl group, an alkenyl group, an alkynyl group, an aryl group, an amino group, an alkoxy group, an aryloxy group, a heterocyclicoxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a heterocyclicthio group, a sulfonyl group, a sulfinyl group, an ureido group, a phosphoramide group, a hydroxyl group, a mercapto group, a halogen atom, a cyano group, a sulfo group, a carboxyl group, a nitro group, a hydroxamic group, a sulfino group, a hydrazino group, an imino group, a heterocyclic group, a silyl group and a silyloxy group.

3. The transition metal complex according to claim 1, wherein the transition metal complex of Formula I is a compound represented by Formula II:

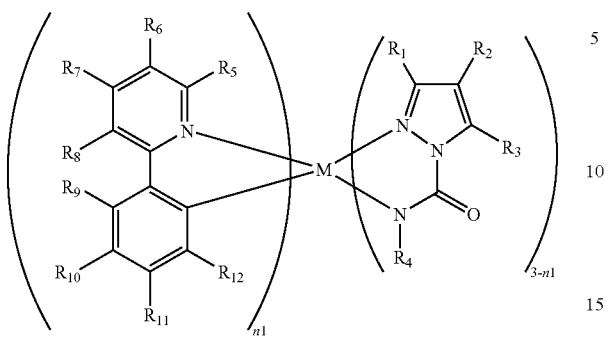

(II)

wherein each of $R_1, R_2, R_3, R_4, R_5, R_6, R_7, R_8, R_9, R_{10}, R_{11}$, and $R_{12}$ is a substituent or a hydrogen atom;
M is a transition metal; and
n1 is 1 or 2.

4. The transition metal complex according to claim 1, wherein the transition metal complex of Formula I is a compound represented by Formula III:

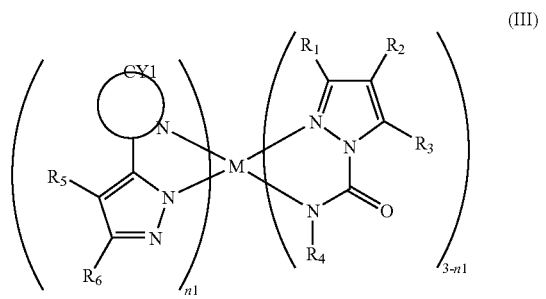

(III)

wherein each of $R_1, R_2, R_3, R_4, R_5,$ and $R_6$ is a substituent or a hydrogen atom;
M is a transition metal;
n1 is 1 or 2; and
CY1 is an aromatic ring or an aliphatic ring.

5. The transition metal complex according to claim 1, wherein the transition metal complex of Formula I is a compound represented by the formula IV:

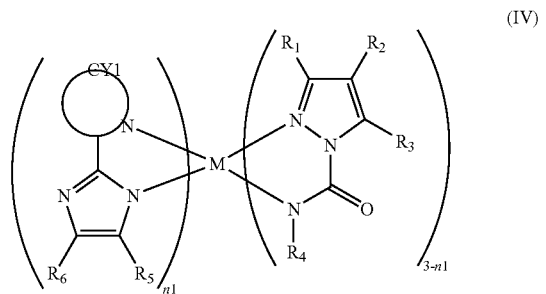

(IV)

wherein each of $R_1, R_2, R_3, R_4, R_5,$ and $R_6$ is a substituent or a hydrogen atom;
M is a transition metal;
n1 is 1 or 2; and
CY1 is an aromatic ring or an aliphatic ring.

6. The transition metal complex according to claim 1, wherein the transition metal complex of Formula I is a compound represented by Formula V:

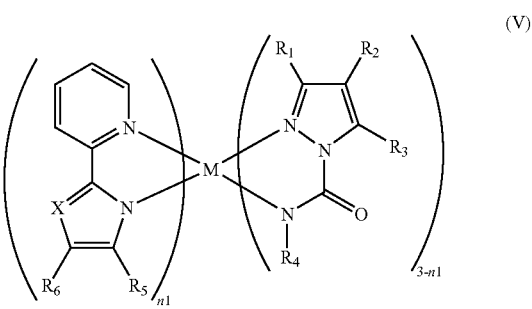

(V)

wherein each of $R_1, R_2, R_3, R_4, R_5,$ and $R_6$ is a substituent or a hydrogen atom;
M is a transition metal;
X is C, N, O, S or P; and
n1 is 1 or 2.

7. The transition metal complex according to claim 1, wherein the transition metal complex of Formula I is a compound represented by Formula VI:

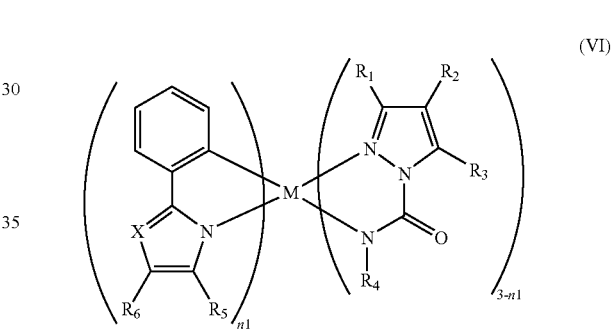

(VI)

wherein each of $R_1, R_2, R_3, R_4, R_5,$ and $R_6$ is a substituent or a hydrogen atom;
M is a transition metal;
X is C, N, O, S or P atom; and
n1 is 1 or 2.

8. The transition metal complex according to claim 1, wherein the transition metal complex of Formula I is a compound represented by Formula VII:

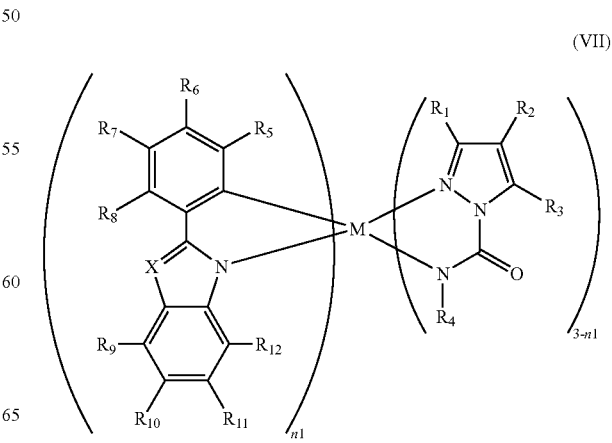

(VII)

wherein each of $R_1, R_2, R_3, R_4, R_5, R_6, R_7, R_8, R_9, R_{10}, R_{11}$, and $R_{12}$ is a substituent or a hydrogen atom;

M is a transition metal;

X is C, N, O, S or P; and n1 is 1 or 2.

9. The transition metal complex according to claim 1, wherein the transition metal complex of Formula I is a compound represented by Formula VIII:

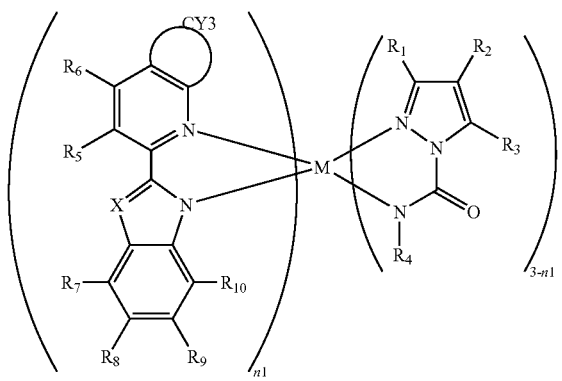

(VIII)

wherein each of $R_1, R_2, R_3, R_4, R_5, R_6, R_7, R_8, R_9$, and $R_{10}$ is a substituent or a hydrogen atom;

M is a transition metal;

X is C, N, O, S or P;

CY3 is an aromatic ring or an aliphatic ring; and n1 is 1 or 2.

10. The transition metal complex according to claim 1, wherein the transition metal complex of Formula I is a compound represented by Formula IX:

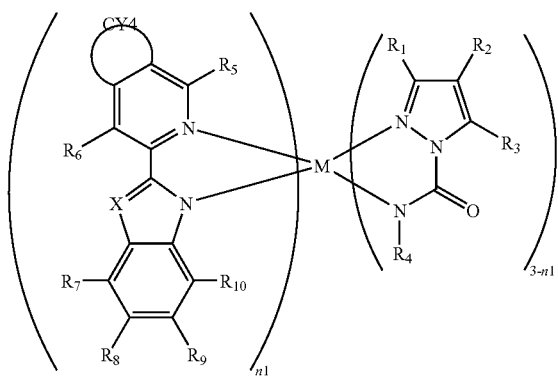

(IX)

wherein each of $R_1, R_2, R_3, R_4, R_5, R_6, R_7, R_8, R_9$, and $R_{10}$ is a substituent or a hydrogen atom;

M is a transition metal;

X is C, N, O, S or P;

CY4 is an aromatic ring or an aliphatic ring; and n1 is 1 or 2.

11. The transition metal complex according to claim 1, wherein the transition metal complex of Formula I is a compound represented by Formula X:

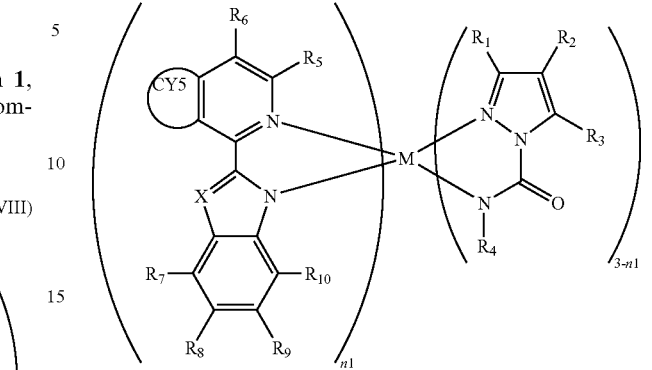

(X)

wherein each of $R_1, R_2, R_3, R_4, R_5, R_6, R_7, R_8, R_9$, and $R_{10}$ is a substituent or a hydrogen atom;

M is a transition metal;

X is C, N, O, S or P;

CY5 is an aromatic ring or an aliphatic ring; and n1 is 1 or 2.

12. The transition metal complex according to claim 1, wherein M is Ru, Rh, Os, Ir, Pt or Au.

13. The transition metal complex according to claim 1, wherein the transition metal complex is one of the compounds represented by the formulae below:

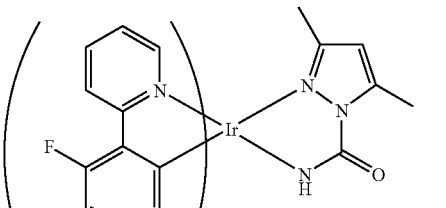

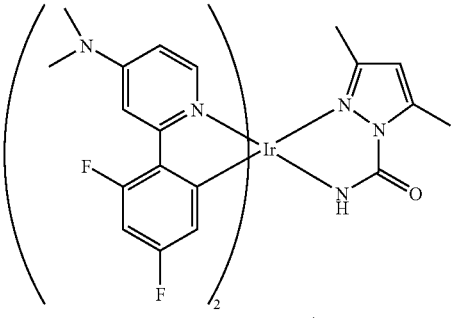

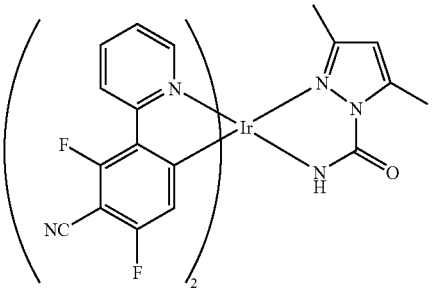

-continued

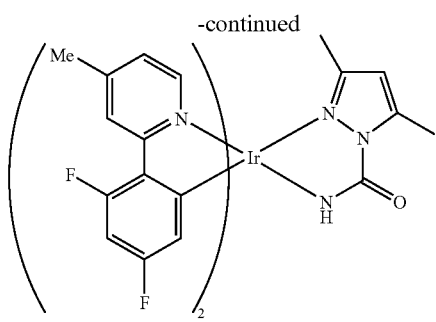

(XI)

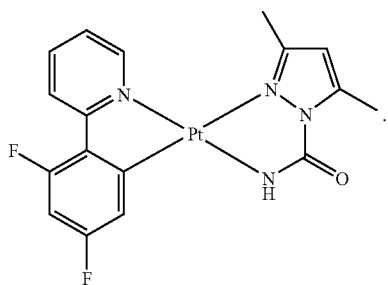

14. An organic electroluminescent display device comprising an organic film having the transition metal complex according to claim 1.

15. An organic electroluminescent display device, comprising:
a pair of electrodes; and
an organic film between the pair of electrodes, the organic film comprising a transition metal complex represented by Formula I:

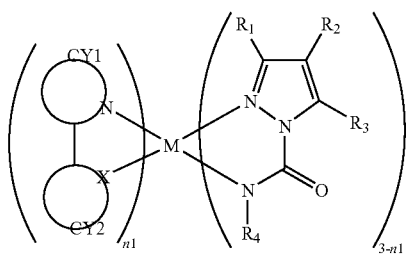

(I)

wherein M is a transition metal;

each of $R_1$, $R_2$, $R_3$ and $R_4$ is a substituent or a hydrogen atom;
X is N or C;
each of CY1 and CY2 is an aromatic ring or an aliphatic ring, and
n1 is 1 or 2.

16. The organic electroluminescent display device of claim 15, wherein the organic film further comprises at least one selected from the group consisting of at least one of polymer hosts, a mixed host of a polymer and a low molecular weight host, a low molecular weight host, and a non-luminescent polymer matrix.

17. The organic electroluminescent display device of claim 15, wherein the organic film further comprises at least one of a green light emitting material and a red light emitting material.

18. An organic electroluminescent display device, comprising:
a pair of electrodes; and
an organic film between the pair of electrodes, the organic film comprising a light-emitting layer comprised of a transition metal complex represented by Formula I:

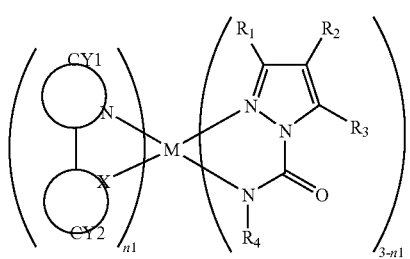

(I)

wherein M is Ru, Rh, Os, Ir, Pt or Au;
each of $R_1$, $R_2$, $R_3$ and $R_4$ is a substituent or a hydrogen atom;
X is N or C;
each of CY1 and CY2 is an aromatic ring or an aliphatic ring, and
n1 is 1 or 2.

19. The organic electroluminescent display device according to claim 18, wherein the amount of the transition metal complex ranges from 1 to 30 parts by weight, based on 100 parts by weight of the total weight of the light emitting layer.

* * * * *